US007622046B2

(12) United States Patent
Rundt et al.

(10) Patent No.: US 7,622,046 B2
(45) Date of Patent: Nov. 24, 2009

(54) MAGNETIC TRANSFER METHOD, A DEVICE FOR TRANSFERRING MICROPARTICLES AND A REACTOR UNIT

(75) Inventors: Kenneth Rundt, Turku (FI); Matti Korpela, Naantali (FI)

(73) Assignee: BioControl Systems, Inc., Bellevue, WA (US)

( * ) Notice: Subject to any disclaimer, the term of this patent is extended or adjusted under 35 U.S.C. 154(b) by 512 days.

(21) Appl. No.: 10/531,464

(22) PCT Filed: Oct. 20, 2003

(86) PCT No.: PCT/IB03/04646

§ 371 (c)(1),
(2), (4) Date: Oct. 13, 2005

(87) PCT Pub. No.: WO2004/035217

PCT Pub. Date: Apr. 29, 2004

(65) Prior Publication Data

US 2006/0118494 A1 Jun. 8, 2006

(30) Foreign Application Priority Data

Oct. 18, 2002 (FI) ................................ 20021870

(51) Int. Cl.
*B01D 35/06* (2006.01)
*B03C 1/28* (2006.01)
*G01N 33/553* (2006.01)

(52) U.S. Cl. ...................... 210/695; 210/222; 335/295; 335/302; 436/526

(58) Field of Classification Search ................. 436/526; 210/222, 695; 335/295, 302
See application file for complete search history.

(56) References Cited

U.S. PATENT DOCUMENTS

| | | | | |
|---|---|---|---|---|
| 2,517,325 | A * | 8/1950 | Lamb | 335/302 |
| 5,942,124 | A | 8/1999 | Tuunanen | 210/695 |
| 6,020,211 | A * | 2/2000 | Tuunanen | 210/222 |
| 6,468,810 | B1 * | 10/2002 | Korpela | 436/526 |

FOREIGN PATENT DOCUMENTS

| | | | |
|---|---|---|---|
| FI | 102906 B | | 3/1999 |
| WO | WO 8705536 A1 | * | 9/1987 |

* cited by examiner

*Primary Examiner*—David A Reifsnyder
(74) *Attorney, Agent, or Firm*—SEED IP Law Group PLLC

(57) ABSTRACT

A magnetic transfer method for sorting, collecting, transferring or dosing microparticles (22) or magnetic particles either in the same liquid (23) or from one liquid (23*a*) into another (23*b*) by using a magnetic field. The transfer device (10) comprises a magnet (13) placed inside a protective coating (21), and the collection or dozing is accomplished by changing the magnetic field of the magnet (13). The changing of the magnetic field is effected by using a ferromagnetic body, such as a plate or tube (12), comprised in the transfer device, in such manner that, when micro-particles are to be collected, the magnet is partially or completely outside the ferromagnetic body and, when the particles are to be released or dozed, the magnet is partially or completely inside or behind the ferromagnetic body.

12 Claims, 26 Drawing Sheets

15
16
13
14
12
11

MAGNETIC TRANSFER METHOD, A DEVICE FOR TRANSFERRING MICROPARTICLES AND A REACTOR UNIT

SUBJECT OF THE INVENTION

The present invention relates to a magnetic transfer method.

BACKGROUND OF THE INVENTION

'Magnetic transfer method' refers to any activity related to particle movements produced by magnetism, such as e.g. sorting, collection, transfer, mixing or dosing of particles in the same liquid or from one liquid to another.

'Particles', 'micro-particles' or 'magnetic particles' refer to any small particles having a diameter mainly in the micrometer range, which can be moved by magnetism. Many different kinds of particles movable by magnetism are known, and the applications using them also vary widely. For example, the size of the particles used in microbiology is generally 0.01-100 μm, usually 0.05-10 μm. Known particles of this type include e.g. particles containing ferromagnetic, paramagnetic or supramagnetic material. Particles may also be magnetic in themselves, in which case they can be moved by means of any ferromagnetic body.

A device designed for the manipulation of micro-particles comprises an element which utilizes magnetism, and which is hereinafter referred to as a magnet. It may be a permanent magnet or an electromagnet which attracts ferromagnetic particles, or a ferromagnetic body which in itself is not magnetic but which still attracts magnetic particles.

The magnet is usually and preferably a round bar magnet. It may also be a bar of some other shape. However, the magnet need not be a bar at all. It may also be a short and wide body or a body of any shape. The magnet may also be composed of several bodies, such as magnets or ferromagnetic bodies.

The magnet has to be covered with a protecting element which protects the magnet from various adverse conditions and enables manipulation of micro-particles, such as binding and releasing. The structure of the protecting element may vary greatly, because it may consist of e.g. a thin film of elastic or stretchable material or even a cup made of hard plastic.

In general, micro-particles are used in solid phase to bind various biomolecules, cell organelles, bacteria or cells. It is also possible to immobilize enzymes on the surface of micro-particles, allowing effective utilization and further use of the enzymes. Most of so-called magnetic nanoparticles (<50 nm) can not be handled by means of ordinary permanent magnets or electromagnets, but they require the use of a particularly high magnetic gradient, as described in specification EP 0842704 (Miltenyi Biotec). Using ordinary permanent or electric magnets, it is usually possible to handle magnetic particles, such as micro-particles having a diametric size of about 0.1 μm or more. The viscosity of the sample may also be a significant factor making it difficult to collect the particles. The particles to be collected may originally have been suspended in a large quantity of liquid, from which a substance to be studied or even cells are desired to be bound to the surface of the particles. It is specifically important to be able to use large initial volumes in applications where components few in number are to be isolated for analysis. For example, efficient concentration of pathogenic bacteria from a large sample volume into a small volume is critical because it has a direct effect on the assay sensitivity and analysis time. At present, there is no sufficiently effective method for accomplishing concentration from a large volume to a small volume by using micro-particles. It would be advantageous to have a process of the above-described type as simple and efficient as possible.

PRIOR ART

Micro-particles manipulated by means of magnets have been used since the 1970's. This technology has been much favored e.g. in immunoassays. The use of micro-particles in immunoassays for separating the bound antigen-antibody complex from the free fraction provided a significant advantage especially in regard of reaction speed. In recent years, the principal development in the utilization of micro-particles has taken place in the areas of molecular biology, microbiology and cellular biology.

In a traditional method, magnetic particles, such as micro-particles present in a reaction solution are captured at a certain point on the interior wall of a tube by means of a magnet placed outside the vessel. After this, the solution is cautiously removed from around the magnetic particles as carefully as possible. In the traditional method, it is the liquids that are actively processed while the magnetic particles remain in the same vessel throughout the entire process.

In another approach, a magnet is used actively to transfer micro-particles. The magnet is inserted into a solution containing micro-particles, so that the magnet attracts the micro-particles in the solution and these form a solid pellet. After this the magnet and the micro-particles can be lifted out from the liquid. The magnet together with the micro-particles can then be immersed in a liquid in another test tube, where the micro-particles can be released from the magnet. In this method, the treatment of the solutions, the pipetting and aspiration phases have been minimized to the extreme.

Patent specification U.S. Pat. No. 2,517,325 (Lamb) describes a solution for collecting metal objects by means of a magnet. The specification describes a long bar magnet which is moved inside an iron tube. The poles of the bar magnet are located at the opposite ends of the longitudinal axis of the physical magnet. By moving the magnet inwards in the iron tube, the magnetic field can be diminished. Similarly, by moving the magnet outwards from the iron tube, the magnetic field is intensified. The specification describes a solution whereby metal objects can be collected at the nose end of a magnet unit. The specification also describes a fixed plastic cover used to protect the magnet.

Patent specification U.S. Pat. No. 2,970,002 (Laviano) describes a solution for collecting metal objects from liquids by means of a magnet. The specification describes a long permanent magnet which collects particles in the nose end part of the magnet unit. The magnet is attached to a metal bar and protected with a separate plastic cover. The specification discloses a process of using the movements of the permanent magnet together with the plastic cover used to protect the magnet. The specification describes the collection of metal objects in the nose part of the magnet unit and dispersion of the metal objects from the surface of the cover by means of a specific design of the plastic cover.

Patent specifications U.S. Pat. No. 3,985,649 (Eddelman), U.S. Pat. No. 4,272,510 (Smith et al.), U.S. Pat. No. 4,649,116 (Daty et al.), U.S. Pat. No. 4,751,053 (Dodin et al.) and U.S. Pat. No. 5,567,326 (Ekenberg et al.) all describe solutions in which a magnetizable material is collected by means of a magnet directly from a solution. A feature common to these specifications is also the fact that the magnets are not protected by separate plastic covers. In these solutions the tip of the magnet has to be washed before the next sampling operation to eliminate the risk of contamination and the carry-over effect.

Patent specification U.S. Pat. No. 5,288,119 (Crawford, Jr. et al.) describes a solution for collecting metal objects by means of a magnet. The magnet of the device according to this specification is not protected with a special cover and is not suited for the collection of metal objects from liquids. The specification describes a solution for the collection of larger metal objects. The specification describes a long bar magnet which is moved inside a non-magnetic tube. This tube has the special property of blocking the magnetic field even though it is itself not magnetic. As alternative materials for this purpose, the specification proposes e.g. bismuth or lead or a mixture of these. The magnet of the device according to this solution is not protected by a special cover and is not suited for the collection of metal objects from liquids.

Application document WO 87/05536 (Schröder) describes the use of a permanent magnet movable inside a plastic cover for the collection of ferromagnetic material from a liquid containing such material. When the magnet is in a low position, ferromagnetic material is collected in the central part a magnet unit. The specification describes the transfer of the ferromagnetic material thus collected into a solution in another vessel and the release of the material from the tip part into the other vessel. The release of the ferromagnetic material is described as being accomplished by means of a design of the plastic cover that prevents the material from moving when the magnet is being moved upwards.

Patent specification U.S. Pat. No. 5,837,144 (Bienhaus et al.) discloses a method for collecting micro-particles by means of a special magnet provided with a plastic protective cover. This specification describes a method for binding micro-particles from a solution which is extracted from a vessel by various arrangements. By moving the magnet, micro-particles can be released from the surface of the plastic cover.

Patent specifications U.S. Pat. No. 5,942,124 (Tuunanen), U.S. Pat. No. 6,020,211 (Tuunanen), U.S. Pat. No. 6,040,192 (Tuunanen), U.S. Pat. No. 6,065,605 (Korpela et al.) and U.S. Pat. No. 6,207,463 (Tuunanen) as well as patent specification US 20010022948 (Tuunanen) also describe devices provided with a plastic protector for the collection of micro-particles from a solution and transferring them into another solution. These specifications mainly describe solutions designed to for the manipulation of micro-particles in very small volumes. Specification U.S. Pat. No. 5,942,124 (Tuunanen) describes a device by means of which micro-particles can be concentrated right at the tip part of a magnet unit. Specification U.S. Pat. No. 6,020,211 (Tuunanen) describes a method of using the device disclosed in the previous specification together with a large so-called traditional magnet for transferring collected micro-particles into smaller vessels. Specification U.S. Pat. No. 6,040,192 (Tuunanen) describes an automated method concerning the use of micro-particles in specific analyses and in the treatment of small volumes. Specification U.S. Pat. No. 6,065,605 (Korpela et al.) describes how the solution disclosed in specification U.S. Pat. No. 5,942,124 (Tuunanen) is applied further to the treatment of fairly large volumes. It describes a method wherein micro-particles are first collected by means of a special magnet unit containing a large magnet. After this, a magnet unit as described in specification U.S. Pat. No. 5,942,124 (Tuunanen) is used to transfer the pellet of micro-particles further into smaller vessels. Specification U.S. Pat. No. 6,207,463 (Tuunanen) likewise describes the application of the above-described magnet unit, by means of which micro-particles can be collected right at the tip part of the device. Application document US 20010022948 (Tuunanen) also describes the manipulation of a very small quantity of micro-particles in special vessels designed for that purpose.

Patent specification U.S. Pat. No. 6,403,038 (Heermann) describes a device comprising a protective plastic cover and a permanent magnet attached to a special bar. The micro-particles are collected at the tip part of the plastic cover, and the method is intended especially for the treatment of small volumes. The bar has a special projecting part which keeps the magnet and the bar in position in the test tube.

Patent EP 1058851 (Korpela) and application document WO 01/60967 (Korpela) describe devices having a stretchable elastomeric protective coating. In these solutions, the micro-particles are collected on the surface of the stretchable protective coating, from where they can be transferred further to another vessel. The protective coating is made of elastomeric material, so that the coating stretched over the magnet is very thin. In this way, the distance separating the magnet from the liquid is minimized.

Patent specification U.S. Pat. No. 5,610,077 (Davis et al.) describes the use of special inner tube together with an outer tube in making specific immunoassays. The specification describes immunoassays performed in a test tube or in a well of a microtiter plate, i.e. microplate, using a special inner tube arrangement with a small liquid volume. Using this tube arrangement, it is possible to raise the liquid surface of the small volume of liquid in the test tube or microplate well, thus producing an enlargement of the reactive surface of the tube and an effective mixing of the solution. This specification makes no mention of micro-particles or concentration from a large liquid volume to a small liquid volume.

None of the above-mentioned patents describe a method whereby micro-particles could be effectively collected from very large liquid volumes and released into a smaller liquid volume. In particular, they describe no realistic way of collecting a large quantity of micro-particles from a large liquid volume. Instead, the above-mentioned specifications describe the treatment of relatively small liquid volumes, such as 5-10 ml, and the treatment of very small liquid volumes. If the objective is to collect proteins, peptides, nucleic acids, cells, bacteria, viruses or other components from a large liquid volume onto the surface of micro-particles, there are certain basic requirements regarding the optimal number of particles to be used. Depending on the micro-particles used, an advantageous amount of particles per milliliter of liquid to be isolated may be at least 107 particles of a diameter of 1-5 μm. The number of particles required increases further if from a given unit volume a desired component very scanty in number is to be bound as reliably as possible.

Especially the method described in specifications U.S. Pat. No. 5,942,124 (Tuunanen), U.S. Pat. No. 6,020,211 (Tuunanen), U.S. Pat. No. 6,065,605 (Korpela et al.), U.S. Pat. No. 6,207,463 (Tuunanen) and EP 0 787 296 (Tuunanen), where the aim is to collect a large amount of micro-particles from a relatively large vessel by means of a small magnet onto the small tip part of a very sharp and narrow bar, is impractical.

A large quantity of micro-particles can not be transferred into a small volume around a small point because the physical dimensions of the pellet formed by the mass of micro-particles grow fast with the liquid volume to be treated. A large mass of micro-particles must be collected either on a large area or in a special recess.

OBJECT OF THE INVENTION

The object of the present invention is to achieve a method and device which do not have the drawbacks described above. The magnetic transfer method of the invention is characterized in that The invention relates in particular to active collection of micro-particles and their transfer from one liquid into another. The method is especially usable in an automatic apparatus in which micro-particles can be treated in various transferring, washing and incubation steps. To the automatic apparatus it is possible to connect units designed e.g. to detect PCR reactions or different labels.

The Transfer Device of the Invention

The invention also relates to a device for the transfer of micro-particles.

An essential technical property of the device of the invention is that the intensity of the magnetic field and its alignment in relation to the surrounding protective coating can be adjusted. This can be implemented by moving the magnet in a ferromagnetic tube so that the magnet can be completely inside the tube, in which situation the power of the magnet is insignificant or nil, or it can be partly or completely outside the tube, in which situation the power and collection surface of the magnet are proportional to the protruding part of the magnet. By combining these properties with the transfer of micro-particles into vessels of suitable size, a very efficient collecting and concentrating process is achieved.

The tube may be made of iron or some other suitable material that has appropriate magnetic properties to prevent leakage of the magnetic flux through the tube. The power of the magnet can be adjusted by varying the position of the magnet relative to the ferromagnetic tube so that part of the magnet is inside the tube. Alternatively, the magnet can be held stationary while the ferromagnetic tube is moved relative to the magnet. The magnet is attached to a bar which may be ferromagnetic or non-ferromagnetic and by means of which the magnet can be moved in the ferromagnetic tube.

The properties and advantages of the ferromagnetic tube described in the invention include at least the following:

1. The tube protects the magnet and its coating from mechanical stress
2. The tube reinforces the structure of the magnet bar and especially the juncture between the tube and the movable pin
3. The tube allows adjustment of the collecting surface and collecting power of the magnet
4. The tube protects external devices sensitive to magnetic fields, especially when the magnet is inside the tube
5. The tube can be used to stretch and/or shape the elastic protective coating.

The magnet may have the shape of e.g. a round bar or pin, but it may also have some other shape. The magnetizing axis of the magnet may also vary. The magnetizing axis may by either longitudinal, in which case it extends in the direction of the longitudinal axis of the bar and the magnetic poles are at the ends of the magnet. Thus, the direction of magnetization is the same as the direction of the ferromagnetic tube, i.e. the direction of movement of the magnet or tube.

However, the magnetizing axis of the magnet may also be transverse, i.e. perpendicular to both the ferromagnetic tube and the longitudinal axis of the bar-like magnet. In this case, the direction of magnetization is perpendicular to the direction of motion of the magnet or tube.

On the other hand, the magnet may also consist of a number of separate magnets, which may be similar or dissimilar to each other and which may be held together by the magnetic force or by a material, which is either ferromagnetic or non-ferromagnetic. The magnet may also consist of a combination of magnetic ferromagnetic materials. The magnet may also be either a permanent magnet or an electromagnet.

By using the magnet arrangement, protective coating and vessels according to the invention, micro-particles can be manipulated very effectively in both large and small liquid volumes. Concentrating the micro-particles in an area close to the tip part of the magnet unit enables both concentration from large volumes and manipulation of micro-particles in small volumes. The invention thus describes a universal solution for both large-scale and small-scale applications involving micro-particles.

The invention provides an optimal solution that is widely usable for the collection and transfer of micro-particles from both large and small liquid volumes. In particular, the invention facilitates the collection of micro-particles from large liquid volumes and their release into small liquid volumes.

The invention describes how, via special shaping of the outer side of the protective plastic or elastomer coating, a sufficient support is achieved for advantageous and reliable collection of a mass of micro-particles around the coating. Special shaping means e.g. grooves, pits and/or protrusions of different sizes and depths. As the micro-particles are collected in the recesses formed by these shapes, the pellet gets special support from the coating against liquid flows and when the magnet unit is being moved. A very significant factor is the effect produced by viscose samples, which in the worst case means that micro-particles do not stay on the surface of the coating but remain in the solution. In the treatment of large volumes, the aforesaid shaping naturally provides a great advantage in respect of reliability of collection.

The device and method described in the invention can be employed in the treatment of very large volumes and, on the other hand, it can also be applied in small volumes. The method is particularly effective when the magnet unit, the vessels to be used with it and the liquid volumes are optimized. Especially the use of the liquid volume displaced by the magnet unit for adjusting the level of the liquid surface is a very effective method during the concentrating stage. For the first time, a device and a method are described wherein the area and intensity of collection of micro-particles and the physical location of the micro-particles can be adjusted according to the needs in each case.

In the invention, a device and a method are described which can be used to collect micro-particles in many different applications. An essential technical solution in the invention is the possibility of controlling by means of the ferromagnetic tube the force of the magnetic field and is application to the surrounding protective coating, around which the micro-particles are collected. The magnet can be moved inwards and outwards relative to the ferromagnetic tube, thereby changing the magnetic field. When the magnet is in an outer position, the protective coating is acted on by a magnetic field of a size corresponding to the portion of the magnet outside the ferromagnetic tube. Micro-particles can then be collected on the outside of the protective coating. When the magnet is moved completely into the ferromagnetic tube, there is no significant magnetic field present in the area outside. In this case, micro-particles do not gather around the protective coating but remain in the solution. The tube may be permanent or adjustable to allow an optimal collection efficiency to be achieved.

The method and device of the invention allow the following solutions and properties:

1. Collection of micro-particles from a large liquid quantity.
2. Collection of a large quantity of micro-particles.
3. Use of the same device in small liquid quantities and in the collection of small quantities of micro-particles.
4. Collection of micro-particles at only one end of the magnet or over the entire surface of the magnet.
5. Collection of micro-particles by using a rigid protective plastic cover.
6. Collection of micro-particles by using a stretchable, elastomeric plastic cover.
7. Utilization of different movements, such as the movements of the magnet or the sleeve around it.
8. Use of different vessels in the concentration.
9. Release of micro-particles into a small liquid quantity.
10. Use of different magnets to create an optimal geometry for the collection of micro-particles.
11. Effective mixing.
12. The test tube or microtiter well is closed by a protective film.

Micro-particles may contain affinity ligands, enzymes, antibodies, bacteria, cells or cell organelles. Binding of desired components can also be produced by selecting the surface properties of the micro-particles to be used and the composition of the buffers in an appropriate manner to advantageously bind desired components from the samples. Examples are ion exchange, hydrophobic and inverse phase chromatography. In these, e.g. the binding and release of proteins from the surface of micro-particles are accomplished by using appropriately selected buffers and solutions. In these cases, very important factors are e.g. salinity and pH.

An affinity ligand may be e.g. a single or double-stranded nucleotide sequence, such as e.g. DNA (Deoxyribonucleic Acid), RNA, mRNA or cDNA (Complementary DNA), or PNA (Peptide Nucleic Acid), a protein, peptide, polysaccharide, oligosaccharide, a small-molecule compound or lectin. The affinity ligand may also be one of the following: Ovomucoid, Protein A, Aminophenyl boronic acid, Procion red, Phosphoryl ethanolamine, Protein G, Phenyl alanine, Proteamine, Pepstatin, Dextran sulfate, EDTA (Ethylenediaminetetraacetic Acid), PEG (Polyethylene Glycol), N-acetyl-glucosamine, Gelatin, Glutathione, Heparin, Iminodiacetic acid, NTA (Nitrilotriacetic Acid), Lentil lectin, Lysine, NAD (Nicotinamide Adenine Dinucleotide), Aminobenzamidine, Acriflavine, AMP, Aprotinin, Avidin, Streptavidin, Bovine serum albumin (BSA), Biotin, Concanavalin A (ConA) and Cibacron Blue.

Immobilizing an enzyme or affinity ligand on micro-particles means that the enzyme or ligand is attached to the surface of the particles or that it is entrapped within a "cage-like" particle, yet so that the surrounding solution can come into contact with it.

An enzyme or ligand can be attached to the micro-particles via a covalent bond, e.g. by means of amino or hydroxy groups present in a carrier. Alternatively, a bond can be created by using a bioaffinity pair, e.g. a biotin/streptavidine pair. According to one procedure, the enzyme to be immobilized is produced by the recombinant DNA technology e.g. in the *Escherichia coli* bacterium and a special affinity tail is made in the enzyme. This affinity tail combines with micro-particles to which has been suitably attached a component that forms a strong bond with the affinity tail in question. The affinity tail may be a small-molecule compound or protein. With such an arrangement, micro-particles could be effectively utilized in the purification of a desired enzyme and at the same time the enzyme bound to the micro-particle would be immobilized on the surface of the micro-particle, ready for use in the method described in the invention.

The enzyme or affinity ligand may also be attached to the micro-particles via non-specific, non-covalent binding, such as adsorption.

The invention concerns a device and method for collecting micro-particles from vessels of widely different sizes and transferring micro-particles from one vessel to another. In particular, the invention describes a device by means of which micro-particles can be collected from a large volume and concentrated into a smaller volume. The concept of "micro-particle" refers in this context to particles preferably having a size of 0.01-100 μm. The micro-particle may also consist of a considerably larger particle, e.g. a particle having a diameter of several millimeters. In the invention, the micro-particles are magnetic, such as e.g. para-, superpara- or ferromagnetic particles or of magnetizable material, or the micro-particles are attached to a magnetic or magnetizable body, and the micro-particles, which may have e.g. affinity groups or enzymes attached to them, are trapped by means of a magnet unit immersed in a first vessel, the magnet unit is moved into another vessel, and the micro-particles are released by the action of the magnet in suitable different ways as described in the invention. Alternatively, the micro-particles need not be specifically detached from the magnet unit.

The magnet used to catch the micro-particles may be either a permanent magnet or an electromagnet. The shape of the magnets may vary depending on the application. The magnetic field may be different in different magnets: a longitudinally magnetized magnet, a magnet magnetized in the direction of the magnet's diameter, or a magnet comprising several magnetic poles in the same body. Individual magnets may also be connected to each other or via suitable ferromagnetic or non-ferromagnetic adapters.

The protective coating may be made of a non-elastic material, such as polypropylene, polystyrene, polycarbonate, polysulphone and polyethylene. The protective coating may also be made of non-ferromagnetic metal or ferromagnetic metal. The protective coating may also be made of an elastomeric material, such as e.g. silicone rubber, fluoroelastomer, polychloroprene, polyurethane or chlorosulfonated polyethylene. The protective coating may also be treated with specific substances, thereby altering the properties of the protective coating. Thus, the protective coating may itself be coated with e.g. teflon (PTFE, Polytetrafluoroethylene). It is particularly important to select the protective material and possible additional treatment in such a way that the final result will allow operation according to the invention even with very strong or corrosive chemicals. The protective coating may also be so shaped that it permits the protection of several separate magnet units, e.g. in devices with 8, 12 or 96 channels. The shape of the protective coating may be either tubular, sheet-like or irregularly shaped. The use of an elastomeric protective coating provides a particularly wide range of possibilities, because in this case the magnet inside and the ferromagnetic tube may also shape the protective coating.

A preferable alternative for the protective coating is a smooth or sheet-like protective sheath of elastic material. This type of protective sheath may be a separate elastic sheath on a special frame. The purpose of the frame is to facilitate the use of the protective sheath and to give the sheath properties allowing stretching. Another alternative is a roll-like embodiment, wherein the protective coating can be changed simply by unrolling new protective coating from a roll. This alternative, too, may comprise the use of a frame, a special support or carrier when the protective coating is being stretched during actual use. The use of this kind of protective coating formed from a single sheet is a very recommendable alternative when the material consumption in the isolating and cleaning processes is to be reduced. The use of a sheet-like protective coating is also economically cheaper than the use of shaped and large protective sheaths produced by means of molding tools.

The use of a sheet-like protective coating in an automatic device is a very simple and effective alternative. When a sheet-like protective coating is used, it is possible to perform an initial stretching by means of a ferromagnetic sleeve during the first stage. At this stage, the magnet still remains inside the ferromagnetic sleeve and the micro-particles outside the protective coating are not exposed to a magnetic field. While the protective coating is held in a stretched state, the magnet can be simultaneously driven out from inside the ferromagnetic sleeve as appropriate. The magnet will now stretch the protective coating still further, causing micro-particles to gather around the protective coating in the area of the pole or poles of the magnet. By moving the magnet inwards or outwards in the sleeve, the solution in the test tube can be mixed by means of the magnet. The mixing can also be performed by moving the ferromagnetic sleeve up and down.

The embodiment described above is particularly advantageous in the manipulation of micro-particles in small vessels, such as micro plates having 96 or 384 wells. The described method of mixing the solution and micro-particles is advantageous because it makes it unnecessary to move the entire device. The mixing is effected by only moving the magnet and/or the ferromagnetic sleeve. The described solution is particularly optimal because no traditional shakers are needed in the process at all. As is well known, traditional shakers are not capable of effectively mixing small amounts of solution, and in particular they are not able to retain the micro-particles in the solution. Thus, a big problem with prior-art devices is fast sedimentation of micro-particles on the bottom of the well.

In the above-mentioned prior-art microplates, in which small liquid volumes are used, evaporation of the liquid during incubations and mixing is also a particularly critical question. By using a protective coating in the described manner according to the invention, micro-particles can also be manipulated in small volumes because the protective coating simultaneously closes the opening of the well, thereby reducing evaporation of the liquid. Therefore, according to the invention, microplates need no more be provided with a separate closing cover of aluminum, rubber or glue tape during mixing and incubation.

Especially when separate protective coatings are used on the transfer devices, the tip part of the protective coating may be shaped in a special way. The shape of the tip part may be designed to achieve a reliable transfer of a maximal amount of micro-particles e.g. from a viscose biological sample into another vessel. When large numbers of micro-particles are collected at the tip part of the elongated protective coating, which is what happens in the case of a permanent magnet magnetized in the longitudinal direction, the outermost micro-particle layers are continuously under the risk of being released and left in the solution. Also, the interfacial tension between the solution and the air is very strong and produces a similar effect tending to release micro-particles.

However, the protective coating can be so shaped that the micro-particles will adhere as strongly as possible to the protective coating regardless of the liquid flow occurring during the movements of the transfer device and regardless of the piercing of the liquid surface and the effect of the surface tension at the liquid surface. For this purpose, the tip of the protective coating can be provided with various recesses and protrusions serving to ensure a reliable transfer of the collected micro-particles into another solution. In this case, the protective coating may be made of either stretchable or non-stretchable material.

A protective coating made of stretchable material may be shaped in a special way to ensure that a large number of micro-particles can be reliably collected and transferred from one vessel into another. For this purpose, the edges of the protective coating may be provided with special protrusions and recesses where the micro-particles will gather. In this case it is preferable to use a transversely magnetized magnet, by means of which micro-particles can be collected on a large surface. Via shaping of the protective coating, special structures supporting the masses of micro-particles are created. The shaping is also a means of influencing the disturbing effects of liquid flows and liquid tension. When a stretchable material is used and the coating has areas of different thicknesses, the protrusions and recesses in the protective coating are stretched in different ways. This phenomenon can be effectively utilized both in the releasing of the micro-particles and especially to achieve an efficient mixing of the solution.

When large quantities of micro-particles are to be concentrated into smaller volumes, it is necessary to use efficient mixing to cause the micro-particles to be effectively released from the surface of the protective coating. In the method described, the protective coating itself functions as an element producing mixing and is therefore a very effective device for performing the mixing. In the most preferable case, the protective coating is differently shaped in different parts of it. When the micro-particles are to be collected from a solution, the magnet is moved downwards while the coating is simultaneously stretched. When the coating is being stretched, the special shaping of its surface causes the micro-particles to gather in sheltered or supporting areas on the surface of the protective coating. When the micro-particles are to be released from the protective coating, the magnet is moved upwards into the ferromagnetic sleeve. To ensure the release of the micro-particles, the ferromagnetic sleeve can simultaneously be moved downwards, thus stretching the protective coating, and then upwards again, these movements being repeated in a suitable manner.

At the same time, very effective mixing of the liquid in the vessel is achieved because the expedient shaping of the protective coating functions like an immersed wobble pump. Alternatively, it is also possible to move the magnet downwards so as to stretch the protective coating when it is desired to achieve an effective mixing based on the above-described phenomenon. Moving the magnet instead of the ferromagnetic tube also produces a movement of the micro-particles towards the magnet and towards the surface of the protective coating, thus further enhancing the mixing effect. These aforesaid ways of mixing the liquid can also be used in suitable combinations. Such a mixing method also works when a longitudinally magnetized magnet is used.

The Reactor Unit of the Invention

The invention also relates to a reactor unit for micro-particles. According to a preferred embodiment of the invention, the transfer device of the invention may also constitute a reactor unit, wherein the vessel or reactor may be made of different materials and have varying shapes. The vessel forming a reactor chamber may be provided with one or more apertures for inlet and outlet of liquids. The vessel may comprise an arrangement whereby the liquid to be processed is re-circulated into the vessel for re-processing. The vessel may form part of a larger assembly comprising several vessels of different types and sizes suitably connected to each other.

The ferromagnetic tube described in the invention may consist of an individual tube, a number of tubes together or an arrangement in which individual tubes form a special array of tubes. In an embodiment of the invention, the ferromagnetic tube may be a special ferromagnetic plate with one or more holes in which one or more magnets can move. Such an arrangement provides is particularly advantageous in the treatment of small volumes, e.g. in 8, 24, 48, 96 and 384-well plate formats, such as microplates or equivalent.

Especially in the treatment of very large volumes, it may be preferable to combine several magnet units to form a group of magnet units to further increase the collection surface for large quantities of micro-particles. In addition, advantageous alternatives for the manipulation of large masses of micro-particles can be achieved via shaping of the protective coating.

Using the device disclosed, micro-particles can be collected from several different vessels, or an arrangement can be used wherein the liquid flows as a steady current past the bars. The latter alternative provides the advantage that operations on even large volumes are relatively easy. In both of these cases the basic assumption is that the particles are initially free in a solution, from which they are then collected by the method described in the invention.

According to the invention, several magnet bars may be arranged in a suitable way inside a single protective coating along its inner circumference. This applies in particular to the case of a very large protective coating, which is used in the processing of very large liquid volumes. Another alternative is to use a single very large magnet bar inside a large protective coating.

Another possible solution according to the invention comprises magnet bars for collecting micro-particles and a special device or bar for agitating the liquid surface in the manner described in the invention. This solution enables solutions in which the magnet bars do not move at all but the agitation of the liquid and micro-particles is effected by an element specially designed for that purpose. The vessel or reactor used in such a solution is designed appropriately to satisfy the needs described.

An embodiment of the invention comprises many separate magnet bars, each of which is provided with a separate protective coating. These magnet bars may be grouped in a suitable array, such as e.g. a fan in the form of a row, a circular arc or several nested circular arcs, wherein each bar collects a suitable amount of micro-particles around it.

If such an array is additionally placed in a closed vessel or reactor into which it is possible to add liquid as needed and which can have a separate valve through which the processed liquid can be let out, then the solution thus achieved can be used to process very large liquid volumes. If the reactor type thus described is placed on its side and the magnet system can be rotated with respect to the protective casing of the reactor, then this solution will also provide a mixing function when liquid samples and micro-particles are being manipulated. The micro-particles may also be attached to the magnet bars beforehand or they may be attached onto the protecting cover of the magnet bars in a suitable manner during the process, and thus the active surface in the reactor will be very large. By mixing, the liquid to be processed can be caused to flow between the micro-particles so that the desired components, such as e.g. proteins, will adhere to the micro-particles on the bars. On the other hand, the liquid can be caused to flow between the micro-particles by suitably arranging liquid flows in the vessel or reactor.

The device and method of the invention are not limited to e.g. molecular biology or purification of proteins, but they can be applied generally in fields where ligands bound to micro-particles can be used to synthesize, bind, isolate, purify or concentrate desired components from different samples: diagnostic applications, biomedicine, pathogen enrichment, synthetization of chemicals, isolation of bacteria and cells.

Practical Applications of the Invention

The device of the invention are applicable for us in a very wide range of areas of application, e.g. in the fields of protein chemistry, molecular biology, cellular biology and proteomics. The invention can be applied in industry, diagnostics, analytics and research.

In the purification of proteins, there is a need to carry out purification tests in small volumes and, on the other hand, to increase the capacity to very large volumes. Using the invention described, it is possible to carry out protein purification operations from different sample volumes as necessary. Protein chemists need to be able to purify proteins from samples having undergone as little pretreatment as possible, such as e.g. from cell lysates. It is also important to be able to vary the purification capacity according to varying needs. Today this is possible by changing the column sizes used. As the purification procedure is advancing, concentration of protein is one of the central operations. In practice, this means reducing the liquid volume without significant loss or denaturation of proteins. At present, the most commonly used methods are dialysis or filtering. Both methods are very time-consuming. The device and method described in the present invention provide in the protein field a versatile method that is applicable for use with varying sample volumes. The capacity can be easily varied without acquiring or making new columns. Simply a larger number of micro-particles is selected for a larger sample volume and, after the binding of the proteins, the micro-particles and protein are collected from the solution by the device and method described in the invention. The washing operations can be carried out either in the same vessel or by changing the vessel. In the former case, the used washing buffers have to be removed from the vessel and replaced with a new washing buffer. The change of buffer can also be effected by using various valve arrangements or suction arrangements. After the washing operations, it is possible, if desirable, to release the proteins bound to micro-particles into a small volume and concentrate the protein solution effectively. Depending on the need, the reduction of the volume can be effected in a stepwise manner towards a smaller volume.

Using the device and method of the invention, it is possible to do e.g. ion exchange chromatography, reverse phase chromatography, hydrophobic chromatography and affinity-chromatographic purification operations. Even gel filtering is feasible by using the device described, but that requires carrying out the actual gel filtering e.g. in a column and then collecting the micro-particles by means of the device of the invention and expelling the proteins into a small volume. The method enables e.g. removal of salt from samples without much diluting the sample as compared with traditional gel filtering columns.

The use of immobilized enzymes in the processing of various proteins, sugars, fats and different so-called biopolymers is a very important area of application of the invention disclosed. An important feature as compared with the use of soluble enzymes is the fact that immobilized enzymes can be easily reused. The disclosed invention makes it very easy to effectively wash an immobilized enzyme for further use.

Below are a few examples of central enzyme groups and individual enzymes used e.g. in industry:

CARBOHYDRASES: Alpha-Amylases, Beta-Amylase, Cellulase, Dextranase, A-Glucosidase, Alpha-Galactosidase, Glucoamylase, Hemicellulase, Pentosanase, Xylanase, Invertase, Lactase, Pectinase, Pullulanase PROTEASES: Acid Protease, Alkaline Protease, Bromelain, Ficin, Neutral Proteases, Papain, Pepsin, Peptidases, Rennin, Chymosin, Subtilisin, Thermolysin, Trypsin LIPASES AND ESTERASES: Triglyceridases, Phospholipases, Esterases, Acetylcholinesterase, Phosphatases, Phytase, Amidases, Aminoacylase, Glutaminase, Lysozyme, Penicillin Acylase ISOMERASES: Glucose Isomerase, epimerases, racemases OXIDOREDUCTASES: Amino Acid Oxidase, Catalase, Chloroperoxidase, Glucose Oxidase, Hydroxysteroid Dehydrogenase, Alcohol dehydrogenase, Aldehyde dehydrogenase, Peroxidases LYASES: Acetolactate Decarboxylase, Aspartic Beta-Decarboxylase, Fumarase, Histidase, DOPA decarboxylase TRANSFERASES: Cyclodextrin Glycosyltranferase, Methyltransferase, Transaminase, Kinases

LIGASES

PHOSPHATASES: Alkaline Phosphatase

The use of enzymes is a very common practice in many branches of industry, as for example: processes of synthesis and modification of lipids, proteins, peptides, steroids, sugars, amino acids, medical substances, synthetic polymers, odorizers, chemicals and so-called chiral chemicals.

Various synthesizing and cutting enzymes used in glygobiology, such as e.g. endoglycosidases and exoglycosidases, are also comprised in the sphere of the invention. Likewise, enzymes familiar from applications of molecular biology, such as restriction enzymes, nucleases, ribozymes, polymerases, ligases, inverse transcriptases, kinases and phosphatases are included in the sphere of the method described in the invention. Examples of DNA/RNA modifying enzymes are: CIAP (Calf Intestinal Alkaline Phosphatase), *E. Coli* alkaline phosphatase, exonucleases (e.g. P1 nuclease, S1 nuclease), ribonucleases, RNases (e.g. Pancreatic RNase, RNase H, RNase T1, RNase M, RNase T2), DNA ligases, RNA ligases, DNA polymerases, Klenow enzyme, RNA polymerases, DNA kinases, RNA kinases, terminal transferases, AMV reverse transcriptase and fosfodiesterases. These and other DNA/RNA modifying enzymes are used in very diverse ways in both research and applications of molecular biology. In proteomics and protein chemistry, proteases are very important enzymes, examples of which are trypsin, chymotrypsin, papain, pepsin, collagenase, dipeptidyl-peptidase IV and various endoproteinases. Synthetic enzymes, catalytic antibodies and multi-enzyme complexes may also be used in the ways described in the invention. Neither is the use of the invention limited by the use of enzymes and other catalytic components in anhydrous conditions e.g. in organic solvents.

As concrete examples of applications of the invention in the field of molecular biology, the following may be mentioned:

Cloning of DNA Inserts:

The components needed in the cloning of DNA inserts include restriction enzymes, (e.g. EcoR I, Hind III, Bam HI, Pst I, Sal I, Bgl II, Kpn I, Xba I, Sac I, Xho I, Hae III, Pvu II, Not I, Sst I, Bgl I), creating blunt ends (e.g. thermally stable polymerases, Klenow Fragment DNA Polymerase I, Mung Bean nuclease), ligations (e.g. T4 DNA Ligase, *E. coli* DNA Ligase, T4 RNA Ligase), phosphorylation (e.g. T4 Polynucleotide Kinase), dephosphorylation (e.g. CIAP, *E. coli* Alkaline Phosphatase, T4 Polynucleotide Kinase) and deletions (e.g. T4 DNA Polymerase, thermally stable polymerases, Exo III Nuclease, Mung Bean Nuclease)

Synthetizing of cDNA and Cloning:

Reverse Transcriptase, RNase H, DNA polymerase I, T4 DNA polymerase I, *E. coli* DNA Ligase.

Labelling of Nucleic Acids:

5' labelling (e.g. T4 Polynucleotide Kinase), 3' addition (e.g. T4 RNA Ligase), 3' fill-in (e.g. Klenow Fragment DNA Polymerase I, T4 DNA Polymerase), 3' exchange (e.g. T4 DNA Polymerase, thermally stable polymerases), nick-translation (e.g. *E. coli* DNA Polymerase I, thermally stable polymerases), replacement synthesis (e.g. T4 DNA Polymerase, thermally stable polymerases, Exo III Nuclease), random priming (e.g. Klenow Fragment DNA Polymerase I, thermally stable polymerases) and RNA probes (e.g. T7 RNA Polymerase, SP6 RNA Polymerase).

Sequencing of Nucleic Acids:

Sequencing of DNA (e.g. *E. coli* DNA Polymerase I, Klenow Fragment DNA Polymerase I, thermally stable polymerases) and sequencing of RNA (e.g. Reverse Transcriptase, thermally stable inverse transcriptases).

Mutagenation of Nucelic Acids:

Oligonucleotide directed (e.g. T4 DNA Polymerase, T7 DNA Polymerase, thermally stable polymerases) and Misincorporation (e.g. Exo III Nuclease, Klenow Fragment DNA Polymerase I, thermally stable polymerases).

Mapping:

Restriction (e.g. Exo III Nuclease), Footprinting (e.g. Exo III Nuclease) and Transcript (e.g. Reverse Transcriptase, Mung Bean Nuclease).

Purification of Nucleic Acids:

Isolation and purification of Genomic DNA, PCR fragments, DNA/RNA probes and plasmid DNA.

DNA Diagnostic Techniques:

DNA Mapping, DNA sequencing, SNP analyses (Single Nucleotide Polymorphism), chromosome analyses, DNA libraries, PCR (Polymerase Chain Reaction), Inverse PCR, LCR (Ligase Chain Reaction), NASBA (Nucleic Acid Strand-Based Amplification), Q beta replicase, Ribonuclease Protection Assay.

DNA Diagnostics:

RFLP (Restriction Fragment Length Polymorphism), AFLP (Amplified Fragment Polymorphism), bacterial infection diagnostics, antibiotic resistancy of bacteria, DNA fingerprints, SAGE (Serial Analysis of Gene Expression) and DNA sequencing.

The disclosed method can also be widely utilized in cell isolation. Relevant cells include stem cells, B-lymphocytes, T-lymphocytes, endothelial cells, granylocytes, Langerhans cells, leucocytes, monocytes, macrophages, myeloid cells, NK (Natural Killer) cells, reticulocytes, trophoblasts, cancer cells, transfected cells and hybridoma cells. The isolation of cells can be implemented using commonly known methods, such as e.g. direct or indirect cell isolation techniques. In the first mentioned direct isolation procedure, the desired cells are collected and separated from the sample by binding them on micro-particles e.g. by utilizing specific antibodies. In the indirect method, instead of the desired cells, all the rest of the cells in the sample are bound fast to the micro-particles. In this case, the desired cells remain in the solution.

The method described in the invention is well applicable for the purification and/or enrichment of bacteria, viruses, yeasts and many other unicellular or multicellular organisms. A particularly important area of application is the enrichment of pathogenic bacteria, such as e.g. *salmonella, listeria, campylobacter, E. coli* O157 and *clostridium*, viruses, parasites, protozoa or other micro-organisms from a large liquid volume. The device and method described in the invention can be utilized in these areas of application as well.

Biocatalysis generally means the use bacteria, enzymes or other components containing enzymes in a process. The enzymes or bacteria may be immobilized on a suitable carrier and the substance to be treated is brought into contact with the immobilized components e.g. by using traditional columns. According to the present invention, cells or enzymes can be suitably attached to micro-particles, which are then used according to the invention to execute different enzymatic reactions.

Isolation of cell organelles and various cell fractions also belongs to the sphere of application of the invention. Cell organelles can be isolated in the normal manner by utilizing e.g. specific antibodies or different affinity ligands.

In the purification of nucleic acids there are widely varying needs, from the purification of quite small amounts of DNA (Deoxyribonucleic Acid), RNA (Ribonucleic Acid) or mRNA (Messenger RNA) to the treatment of large quantities of many liters. By the method according to the present invention, nucleic acids can be effectively isolated from both large and small sample quantities.

By using this method, isolating and purifying processes can be chained according to varying needs. For example, the desired cells can be first isolated from the sample and purified. After this, e.g. cell organelles can be isolated and separated from the cells. The cell organelles are purified and the process can continue e.g. to DNA or protein purification. During the process, micro-particles provided with different coatings and properties can be used alternately according to the needs. The last step is concentration of the purified product into a desired volume.

BRIEF DESCRIPTION OF THE DRAWINGS

FIG. 22 corresponds to FIG. 18 and shows a tube in another situation.

DETAILED DESCRIPTION OF THE DRAWINGS

Figures 1A, 1B, 1C, 1D:
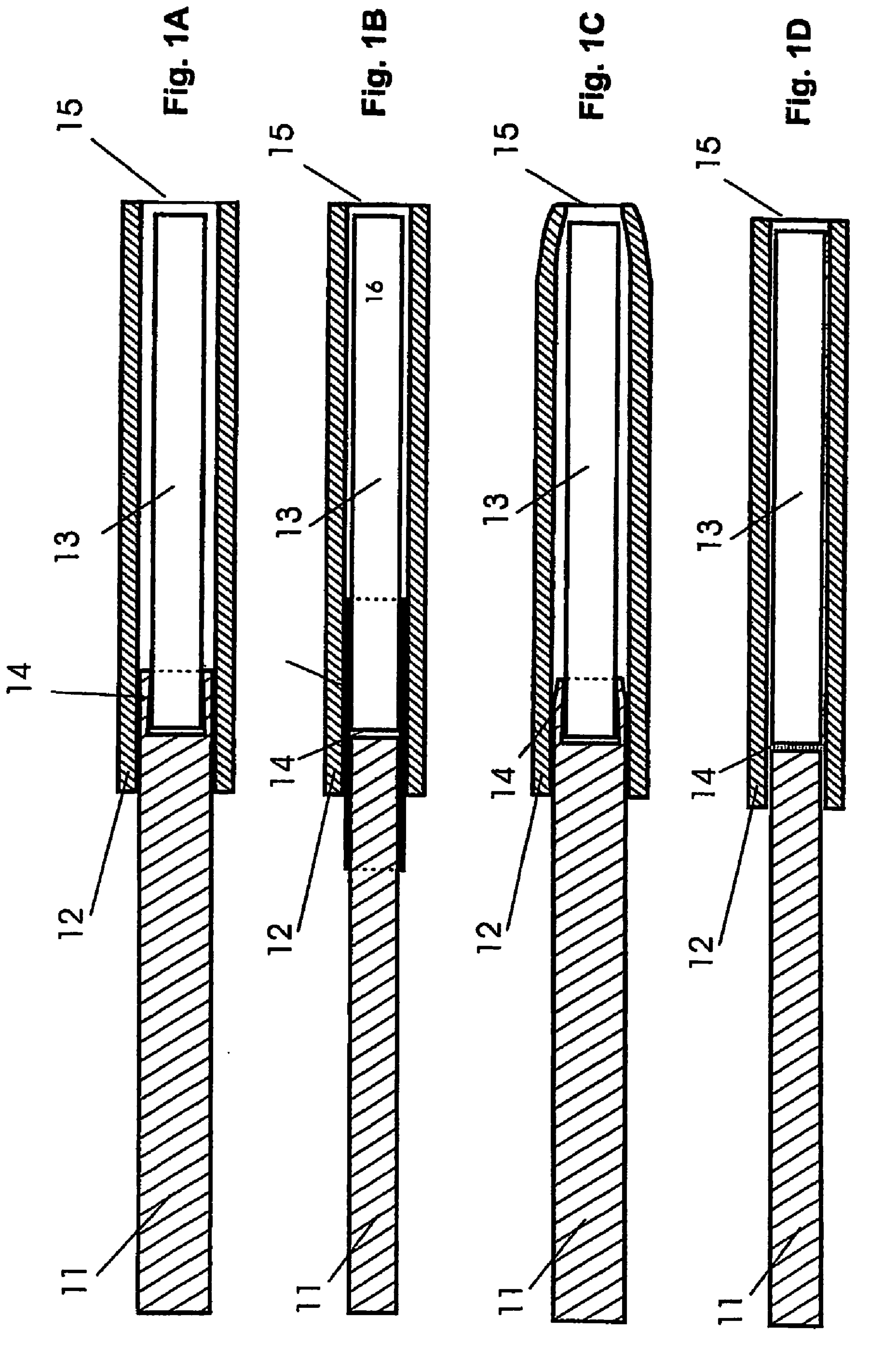
FIG. 1A-1G present diagrammatic and sectioned views of different embodiments of the device of the invention for transferring micro-particles.

FIG. 1A presents an embodiment of the magnet unit 10 of the invention, comprising a ferromagnetic tube or sleeve 12. Placed inside the tube or sleeve is a permanent magnet 13, which is moved by means of a bar or actuating rod 11. The junction between the magnet 13 and the rod 11 is indicated by reference number 14 and the aperture at the end of the tube 12 by reference number 15. By moving the rod 11 and the tube 12 inside it axially relative to each other, the end of the bar magnet 12 is pushed out through the aperture 15 at the end of the tube 12. In other words, the rod 11 and the magnet 13 connected to it can be moved inside the tube 12, or the tube 12 can be moved while the rod 11 and the magnet 13 remain stationary. Alternatively, both parts 12 and 13 may be moved. Using any of these alternative techniques, the magnet 13 can be pushed out through the aperture 15 at the end of the tube 12 and back into the tube 12.

In FIG. 1A, the diameter of the rod 11 is greater than the diameter of the magnet 13. The magnet 13 has been attached to the rod 11 by inserting the end of the magnet 13 into a slot provided at the end of the rod 11. The slot and the end of the magnet 13 are fitted to each other with a close tolerance that keeps the magnet 13 and the rod connected together. As the inner diameter of the ferromagnetic tube 12 in this solution is greater than the diameter of the magnet 13, this may be a disadvantage in some cases.

FIG. 1B presents a second embodiment of the magnet unit 10, wherein the magnet 13 and the rod 11 have equal diameters. The connecting element between the magnet 13 and the rod 11 is a thin-walled sleeve 16, into which the ends of both the rod 11 and the magnet 13 are inserted. The inside diameter of the thin-walled sleeve 16 has been so designed that the fit between the sleeve 16 and the magnet 13 and the fit between the sleeve 16 and the rod 11 are sufficiently tight to keep these parts connected together. As the sleeve 16 has a thin-walled structure, the diameter of the magnet 13 may be nearly equal to the inside diameter of the ferromagnetic tube 12.

FIG. 1C presents a third embodiment of the magnet unit 10, wherein the ferromagnetic tube 12 has a constricted end aperture 15. In this way, a suitable clearance between the magnet 13 and the tube 12 is achieved even if the inside diameter of the sleeve 16 should be clearly larger than the diameter of the magnet 13.

FIG. 1D presents a fourth embodiment of the magnet unit 10, wherein the junction 14 between the magnet 13 and the rod 11 is implemented using glue. In this solution, the magnet 13 and the rod 11 have equal diameters, allowing a suitable small clearance between these parts and the inner surface of the tube 11 to be made achieved.

Figures 1E, 1F, 1G:
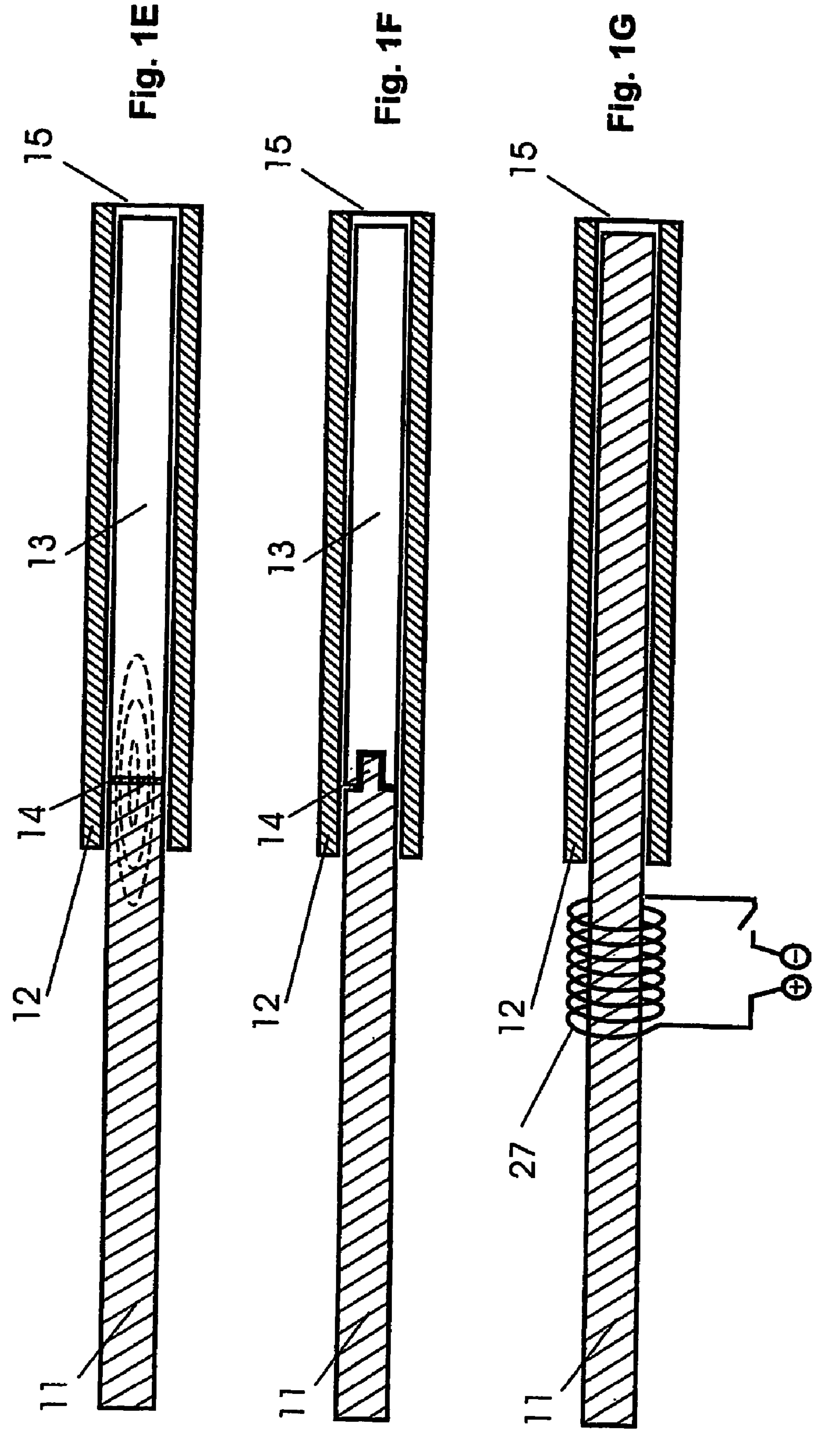

FIG. 1E presents a fifth embodiment of the magnet unit 10, wherein the magnet 13 and the rod 11 are connected to each other by the magnet's 13 own magnetic force, so that the magnet 13 attracts the rod 11 into a tight contact with the magnet 13. This solution is feasible only if the rod 11 is made of a ferromagnetic material. In this solution, too, the magnet 13 and the rod 11 have equal diameters.

FIG. 1F presents a sixth embodiment of the magnet unit 10, wherein the end of the rod 11 is provided with a protrusion, which is inserted into a slot formed in the end of the magnet 13. At the junction 14, the fit between the protrusion and the slot has been made tight enough to keep these parts connected together.

FIG. 1G presents a seventh embodiment of the magnet unit 10, in which an electromagnet is used instead of a permanent magnet. In this solution, the rod 11 is made of a ferromagnetic material and it has a winding 27 placed around its one end. The winding induces a magnetic field in the rod 11 when a voltage source is connected to the winding 27. Thus, the rod 11 functions as an electromagnet, requiring no separate permanent magnet connected to it.

Figure 2A:
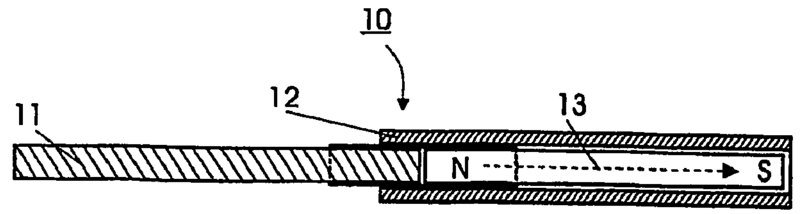
FIG. 2A-2G present diagrammatic views of different embodiments of the magnets of the magnet unit and their magnetic fields.

FIG. 2A presents an embodiment of the magnet unit 10 in which the magnet 13 is mounted in a manner corresponding to the solution in FIG. 1B, in other words, the magnet 13 is connected to the rod 11 by means of a sleeve. However, in the case of FIG. 1B there was no mention about the direction of magnetization of the magnet. In the magnet unit 10 in FIG. 2A, the magnet 13 is magnetized in the direction of the longitudinal axis of the magnet 13.

Figure 2B:
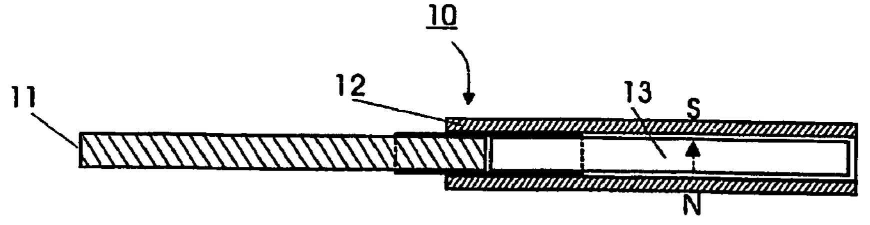

The embodiment of the magnet unit 10 presented in FIG. 2B corresponds to the solution in FIG. 2A in other respects except that the magnetization direction of the magnet 13 is transverse, i.e. perpendicular to the longitudinal axis of the magnet 13. However, in both FIG. 2A and FIG. 2B, the magnet 13 can also be connected to the rod 11 in any other way.

FIG. 2C-2G present diagrams representing the magnetic field produced by the magnet 13 of the magnet unit 10 in different embodiments.

Figure 2C:
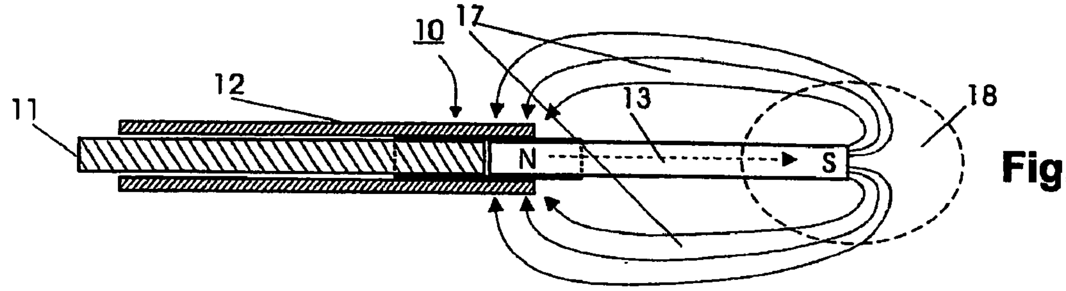

The magnet 13 of the magnet unit 10 presented in FIG. 2C is magnetized longitudinally as in FIG. 2A. In the situation represented by FIG. 2C, one end of the magnet 13 is partially projecting out of the tube 12, so its magnetic field 17 extends from the farther end of the magnet 13 to the end of the tube 12. With this solution, the greatest magnetic flux density occurs around the free end of the magnet 13, this area being indicated in FIG. 2C by reference number 18. With the solution described, most of the micro-particles are caused to gather only at this end of the magnet 13, so the quantity of micro-particles to be collected is limited.

Figure 2D:
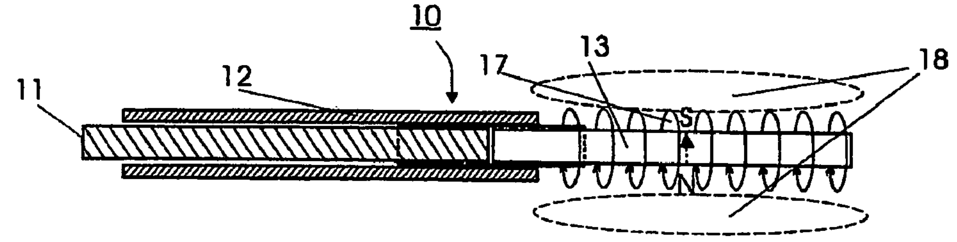

FIG. 2D shows the magnetic field of the magnet 13 of the magnet unit 10 in the case when the magnetizing axis of the magnet 13 is transverse, i.e. in accordance with FIG. 2B. In this case, the magnetic field 19 generated is uniformly distributed over the whole magnet 13, providing a maximal collecting surface for the collection of micro-particles.

Figure 2E:
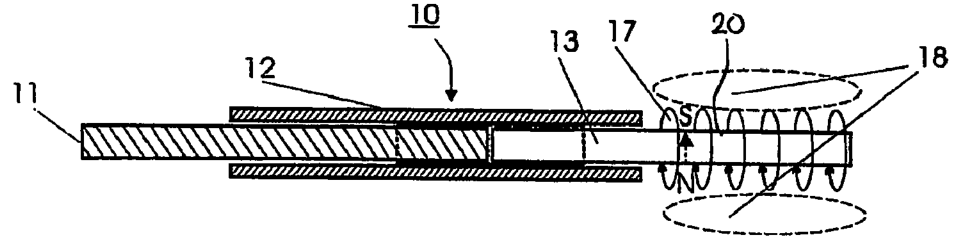

However, if it is desirable to reduce the collecting surface of the magnet 13 of the magnet unit 10, the magnet 13 can be left partially inside the ferromagnetic tube 12. Such a situation is illustrated in FIG. 2E. In this case, the collecting surface 20 of the magnet 13 is somewhat smaller than in the situation illustrated by FIG. 2D.

Figure 2F:
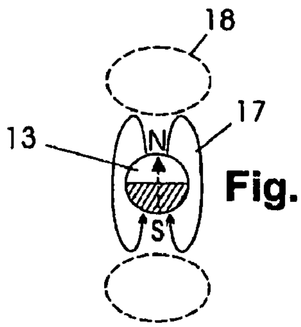
Figure 2G:
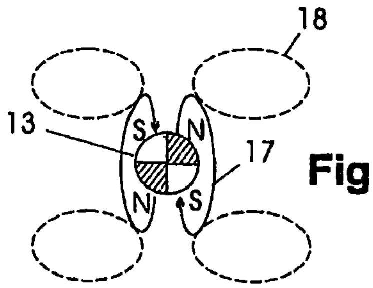

FIGS. 2F and 2G present diagrammatic sectional views of two magnets 13 of the magnet unit 10, which are magnetized transversely in two different ways. In FIG. 2F, the magnet 13 is divided into two parts by a plane in the direction of longitudinal axis. In FIG. 2G, the magnet 13 is correspondingly divided into four longitudinal parts. From FIGS. 2F and 2G it can be seen that the magnetic fields are different in the two cases because the magnetic fields are disposed in slightly different ways. However, both solutions and all their variations are equally usable.

Figure 3B:
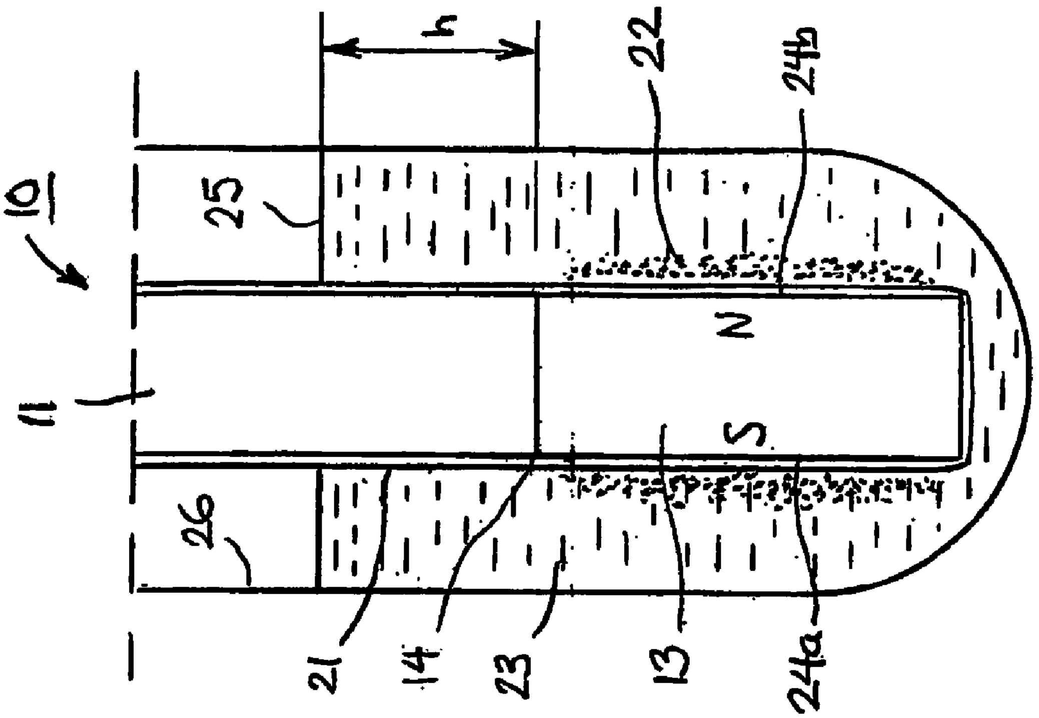
FIGS. 3A and 3B present diagrammatic views of embodiments of the magnet unit placed in a solution containing micro-particles.
Figure 3A:
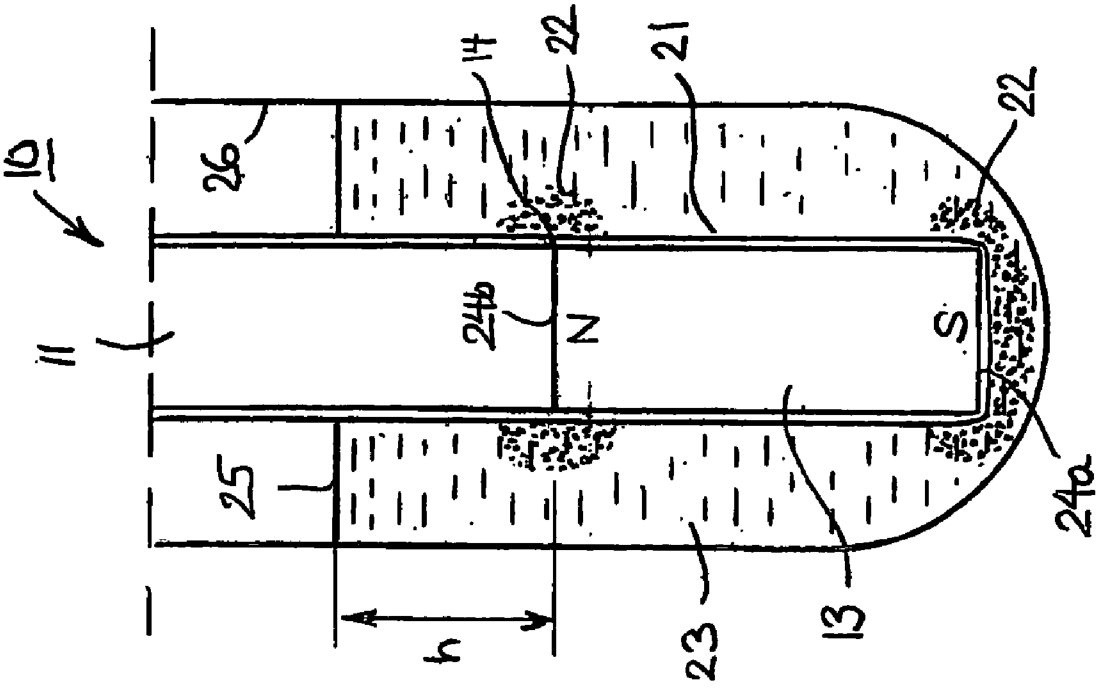

FIG. 3A presents a magnet unit 10 for the collection of micro-particles 22 from a solution in a vessel 26, such as a test tube. A magnet 13 protected with a protective coating 21 is attached to a rod 11, which is non-ferromagnetic. In FIG. 3A, the magnet 13 is completely below the liquid surface 25, the distance of the magnet 13 from the liquid surface 25 being h. The magnet 13 in FIG. 3A is magnetized in the direction of the longitudinal axis of the magnet 13. The micro-particles 22 in the solution 23 in the vessel 26 now gather outside the protective coating 21 around the two poles 24*a* and 24*b* of the magnet 13, both at the tip part of the protective coating 21 and at the junction 14 between the rod 11 and the magnet 13. This is a normal situation when the magnet 13 is completely below the liquid surface 24 of the solution 23.

FIG. 3B presents a second embodiment of the magnet unit 10, which also comprises a magnet 13 provided with a protective coating 21 and completely immersed below the liquid surface 25 at distance h from the liquid surface 25. This embodiment corresponds to the embodiment presented in FIG. 3A in other respects except that the magnet 13 is magnetized in the transverse direction. From FIG. 3B one can see that the micro-particles 22 now gather in a large area outside the protective coating 21. However, it would be preferable to have all the micro-particles 22 collected at just the lower part of the tip of the magnet unit 10. This is especially advantageous when the micro-particles 22 are to be transferred into a small liquid volume. In FIG. 3B, the micro-particles 22 do not gather in a small area and in particular not in the area around the lower part of the protective coating 12. Therefore, this alternative is not very advantageous when micro-particles 22 are to be concentrated into small liquid volumes.

Figure 4B:
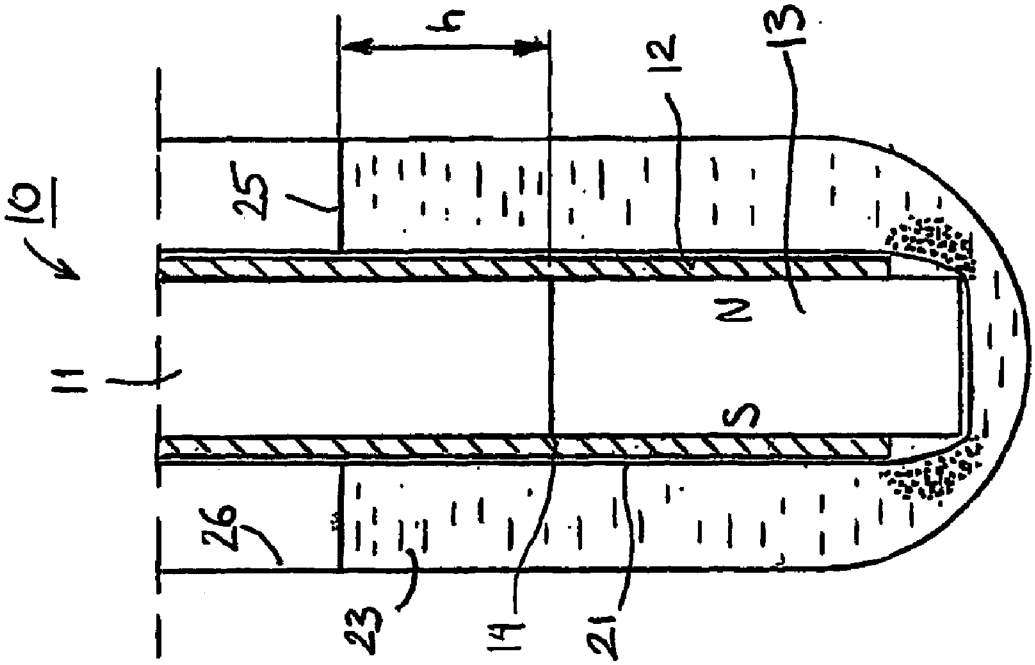
FIG. 4A-4B correspond to FIGS. 3A and 3B and present other embodiments of the magnet unit in a solution.
Figure 4A:
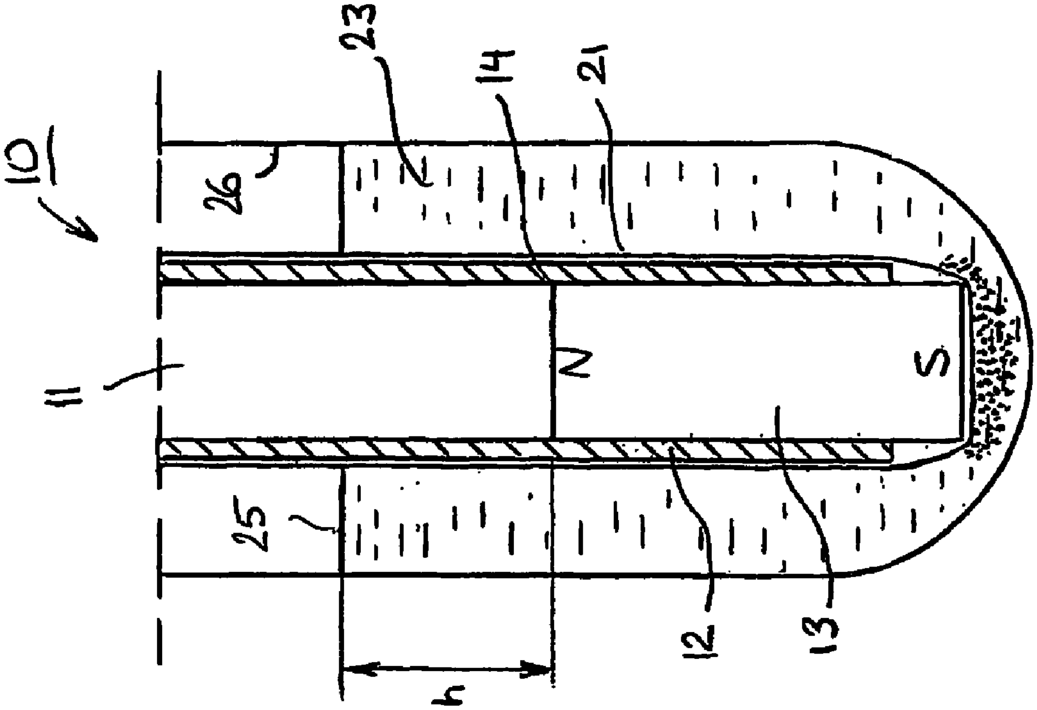

FIG. 4A presents a magnet unit 10 placed in a solution 23 in a test tube 26 and its shows how the micro-particles 22 gather at the lower part of the magnets 13 of the magnet unit 10, which are protected with a protective coating 21. In FIG. 4A, the magnet 13 and both of its magnetic poles 24*a* and 24*b* are completely below the liquid surface 25. However, the micro-particles 22 only gather in the lower part of the protective coating 21 because the upper pole 24*b* of the magnet 13 has been shorted by pushing a ferromagnetic tube 12 in a suitable manner over the magnet 13. There is no magnetic field outside the ferromagnetic tube 12 around the upper pole 24*b* of the magnet 13, which is why no micro-particles 22 appear outside the protective coating 21. Using the magnet unit 10 described, micro-particles 22 can be concentrated into small liquid volumes even when the magnet 13 is completely below the liquid surface 25 and fastened to a non-ferromagnetic rod 11.

In the situation represented by FIG. 4A, when the magnet 13 is moved to a position completely inside the ferromagnetic tube 12, the magnetic field of the magnet 13 disappears almost completely. The micro-particles 22 can thus be released from the surface of the protective coating 21 simply by only pushing the magnet 13 completely into the ferromagnetic tube 12. Micro-particles 22 adhering to the surface of the protective coating 21 can be transferred from vessels 26 to other vessels while the magnet 13 is kept suitably outside the ferromagnetic tube 12.

FIG. 4B presents a magnet unit 10 corresponding to the embodiment in FIG. 4A in other respects except that the magnet is transversely magnetized. In FIG. 4B, the magnetic field of the transversely magnetized magnet 13 has been reduced by means of a ferromagnetic tube 12. In the situation illustrated by FIG. 4B, a very small part of the magnet 13 remains outside the ferromagnetic tube 12. From FIG. 4B it can be seen that by using a transversely magnetized long magnet 13 and a protective sleeve 12, the micro-particles 22 can be concentrated in a simple manner right at the lower part of the protective coating 21. Thus, both FIGS. 4A and 4B represent advantageous and effective methods and devices for the manipulation of micro-particles in small liquid volumes.

FIG. 5A-5E illustrate different steps of a process of collecting micro-particles 22 from a solution 23 by means of a magnet unit 10 provided with a non-stretchable protective coating. The magnet 13 and the ferromagnetic tube 12 can be moved axially relative to each other and the magnet 13 is magnetized in the direction of its longitudinal axis.

FIG. 5A-5E also illustrate different ways of concentrating the micro-particles right at the lower part of the protective coating 21 by means of a ferromagnetic tube and a magnet 13 and releasing them e.g. into small liquid volumes.

Figure 5A:
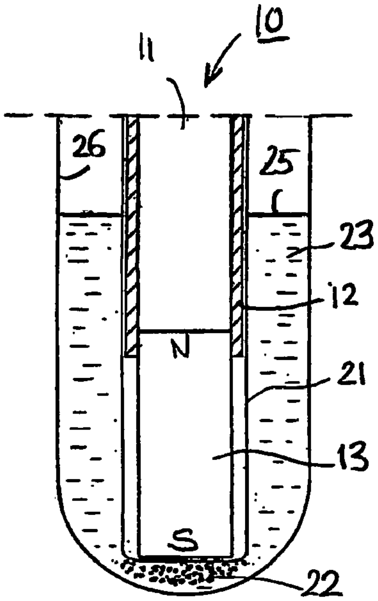
FIG. 5A-5E present embodiments of a magnet unit provided with a non-stretchable protective coating and a longitudinally magnetized magnet, placed in a solution.

FIG. 5A presents a magnet unit 10 in which the magnet 13 has been pushed out from the ferromagnetic tube 12 by means of a non-ferromagnetic rod 11, so that the magnetic field of the magnet 13 is mainly in the lower part of the protective coating 21. Therefore, the micro-particles 22 gather at the lower part of the protective coating 21. In the following examples, too, the rod 11 moving the magnet is non-ferromagnetic.

Figure 5B:
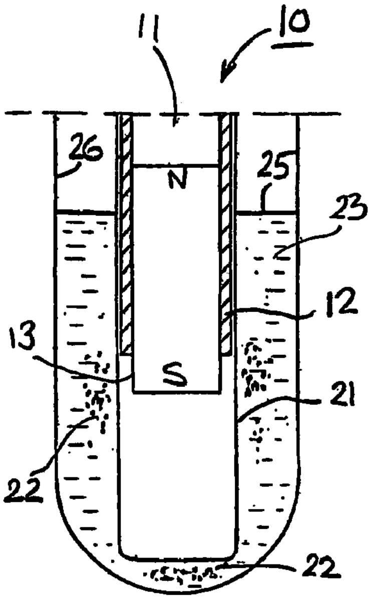

FIG. 5B presents the magnet unit 10 of FIG. 5A with the magnet 13 in a different position. In FIG. 5B, the magnet 13 has been moved nearly completely into the ferromagnetic tube 12 while the tube remains stationary. In this case, some of the micro-particles 22 in the solution 23 move upwards along the protective coating 21.

Figure 5C:
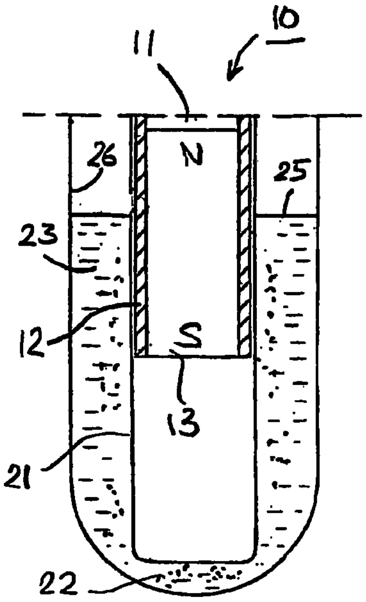

FIG. 5C presents the magnet unit 10 of FIG. 5B with the magnet 13 completely retracted into the tube 12, the micro-particles being now dispersed in the solution 23. Therefore, when the magnet 13 is moved upwards from the lower part of the protective coating 21, the magnetic field is not optimal for collecting micro-particles 22 in the lateral area of the protective coating 21. This is due to the position of the magnetic field and magnetic poles of the magnet 13 and their attraction relative to the protective coating 21 used. Thus, this arrangement is a usable but not the most advantageous alternative for releasing the micro-particles from the surface of the protective coating 21. However, by optimizing the micro-particles and the speed of upward movement of the magnet 13, it is possible to achieve a good final result, in other words, the micro-particles remain right at the lower part of the protective coating 21.

Figure 5D:
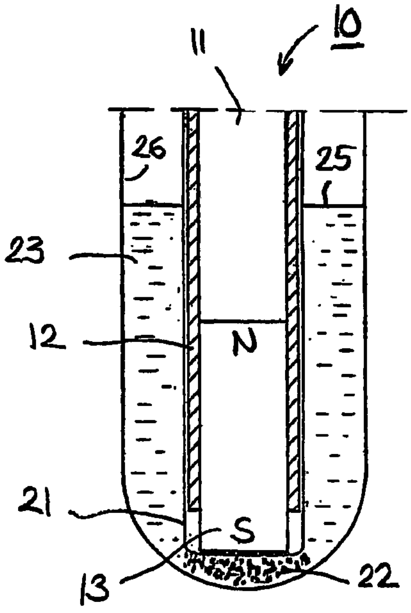

FIG. 5D illustrates an alternative and effective way of releasing the micro-particles 22 in a controlled manner from the lower part of the protective coating 21 of the magnet unit 10 shown in FIG. 5A and transferring them e.g. into small volumes. In FIG. 5D, instead of moving the magnet 13 upwards as in FIG. 5B, the ferromagnetic tube 12 is now moved downwards. As shown in the figure, the micro-particles 22 do not move upwards along the protective coating 21.

Figure 5E:
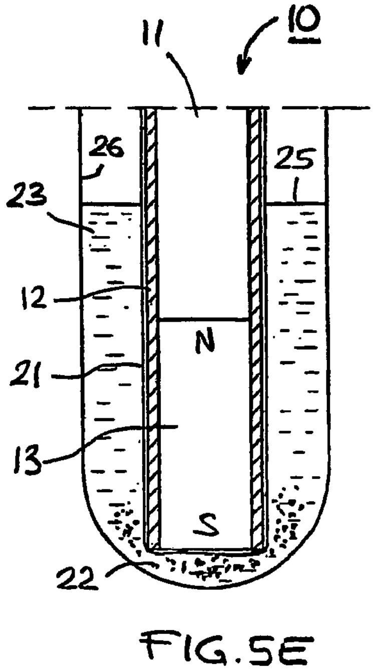

FIG. 5E presents the magnet unit 10 of FIG. 5D with the ferromagnetic tube 12 moved completely over the magnet 13. As shown in the figure, the micro-particles 22 now remain better in place in the solution 23 in the lower part of the test tube 26 near the end of the magnet unit 10.

However, neither one of the procedures illustrated in FIG. 5B-5C or FIG. 5D-5E is very advantageous in the collection and manipulation of very large masses of micro-particles.

FIGS. 6A-6E illustrate different steps of a process of collecting micro-particles 22 by means of a magnet unit 10 provided with a non-stretchable protective coating 21, wherein the magnet 13 or the ferromagnetic tube 12 is moved and the magnet 13 is transversely magnetized.

Figure 6A:
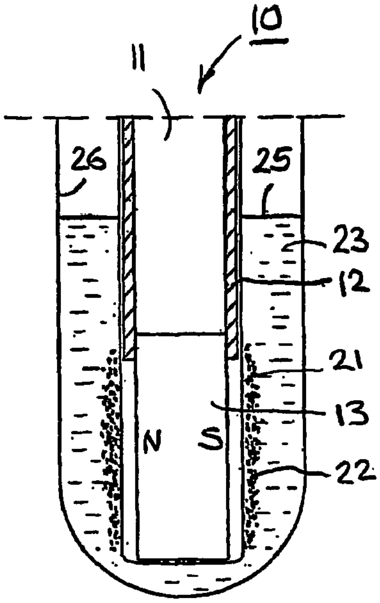
FIG. 6A-6E present embodiments of a magnet unit provided with a non-stretchable protective coating and a transversely magnetized magnet, placed in a solution.

FIG. 6A presents a magnet unit 10 in which the transversely magnetized magnet 13 has been pushed out from the ferromagnetic tube 12, which only covers a small part of the magnet 13. The micro-particles 22 now gather outside the protective coating 21 of the magnet unit 10.

Figure 6B:
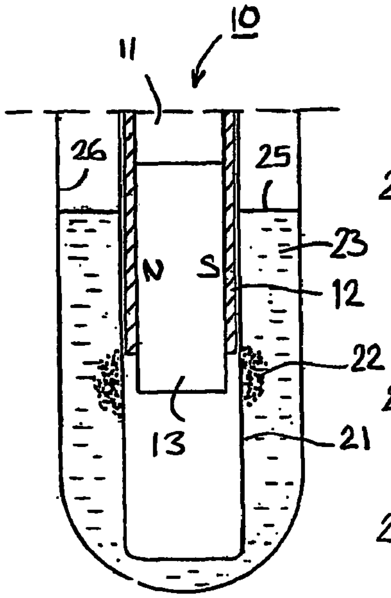

FIG. 6B presents the magnet unit 10 of FIG. 6A in a position where the magnet 12 has been moved upwards almost completely into the ferromagnetic tube 12. Most of the micro-particles 22 around the lower part of the protective coating 21 now move upwards with the magnet 13.

Figure 6C:
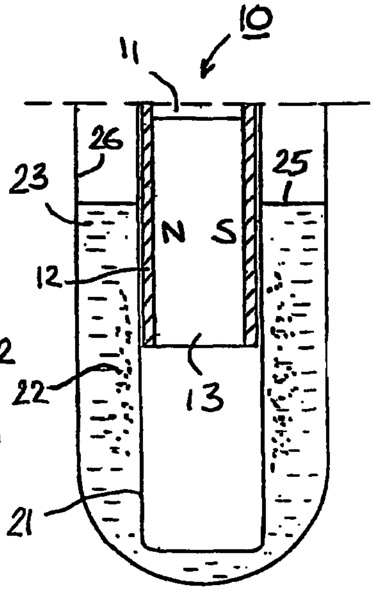

FIG. 6C presents the magnet unit 10 of FIG. 6B in a position where the magnet 13 is completely inside the ferromagnetic tube 12. The micro-particles 22 are now released into the solution 23. Therefore, this procedure is not suited for concentrating micro-particles 22 around the lower part of the protective coating 21 and transferring them e.g. into a small liquid volume.

Figure 6D:
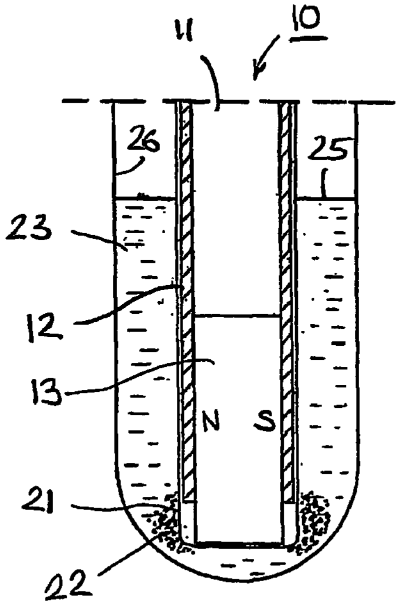

FIG. 6D presents the magnet unit 10 of FIG. 6A in a position where the ferromagnetic tube 12 has been moved downwards so that it almost completely covers the magnet 13.

At the same time, the micro-particles 22 move suitably downwards together with the tube 12.

Figure 6E:
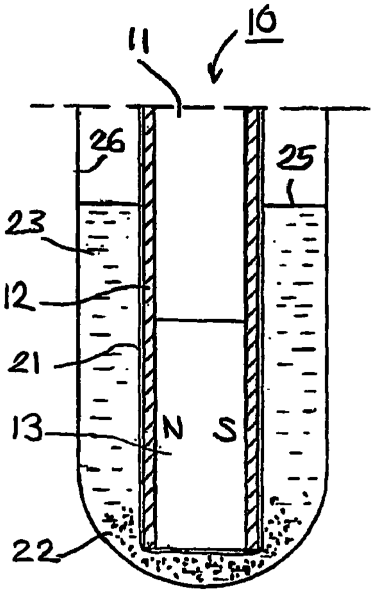

FIG. 6E presents the magnet unit 10 of FIG. 6D in a position where the ferromagnetic tube 12 completely covers the magnet 13. The figure shows that in this way the micro-particles 22 can be effectively concentrated near the lower part of the protective coating 21 of the magnet unit 10. Therefore, this solution is well applicable both for the collection of large quantities of micro-particles and for the concentration of micro-particles into small liquid volumes.

FIGS. 7A-7E illustrate different steps of a process of collecting micro-particles 22 by means of a magnet unit 10 provided with a stretchable protective coating 21 by moving either the magnet 13 or the ferromagnetic tube 12. The magnet 13 is longitudinally magnetized.

Figure 7A:
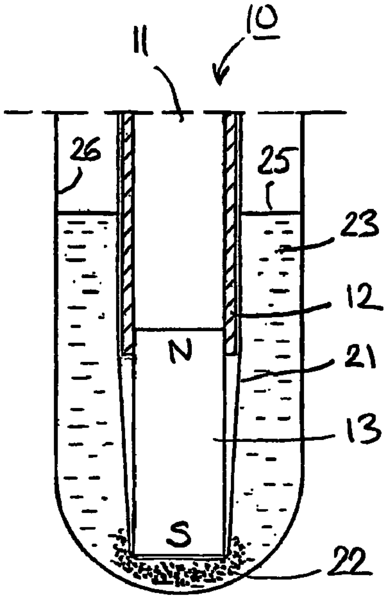
FIG. 7A-7E present embodiments of a magnet unit provided with a stretchable protective coating and a longitudinally magnetized magnet, placed in a solution.

FIG. 7A presents a magnet unit 10 in which a longitudinally magnetized magnet 13 has been pushed out from the ferromagnetic tube 12 so that it simultaneously stretches the stretchable protective coating 21. The micro-particles 22 now gather near the end of the magnet 13 around the lower part of the stretched protective coating 21. Due to the stretching of the protective coating 21, the thickness of the protective coating 21 has been reduced at the same time and the magnetic field has become more intensive as the protective coating 21 has grown thinner.

Figure 7B:
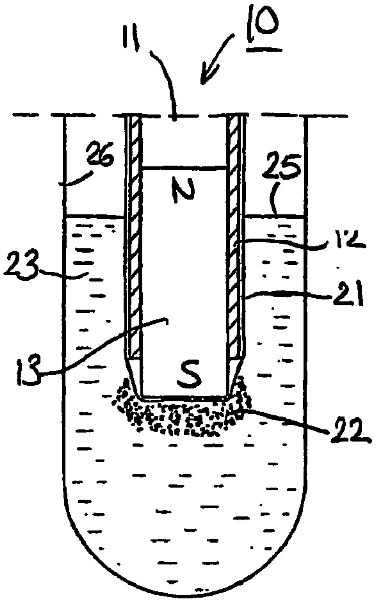

FIG. 7B presents the magnet unit 10 of FIG. 7A in a position where the magnet 13 has been moved upwards into the ferromagnetic tube 12. At the same time, the stretched protective coating 21 contracts upwards. As a result, the magnetic field acting at the lower part of the upwards moving protective coating 21 is still sufficient to keep the micro-particles 22 gathered on the protective coating 21.

Figure 7C:
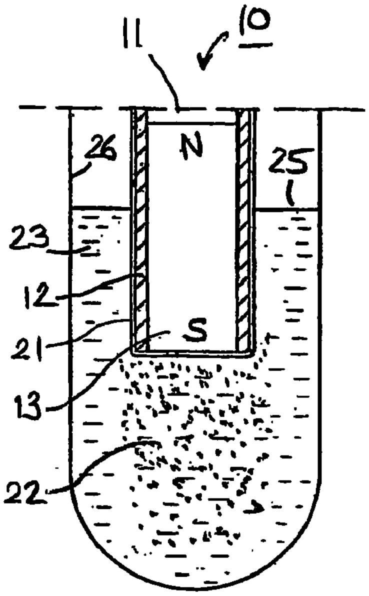

FIG. 7C presents the magnet unit 10 of FIG. 7B in a position where the magnet 13 has been retracted completely into the tube 12 and the micro-particles 22 have been released from the magnetic field. In this way, the micro-particles 22 can be well concentrated near the lower part of the protective coating 21 and transferred further into a small liquid volume.

Figure 7D:
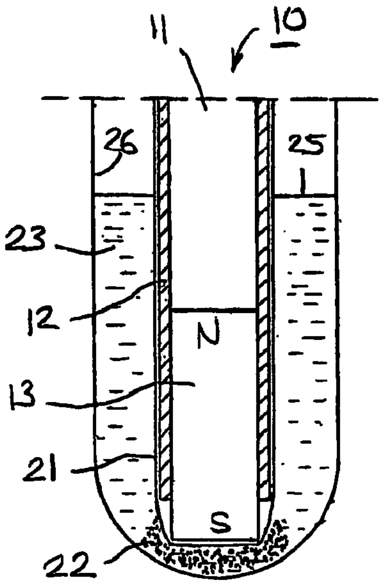

FIG. 7D presents the magnet unit 10 of FIG. 7A in a position where the ferromagnetic tube 12 has been moved downwards over the magnet 13. The magnet 13 does not move but continues keeping the protective coating 21 stretched. Due to the stretching of the protective coating, the magnetic field is very large and the micro-particles 22 adhere very well to the protective coating 21.

Figure 7E:
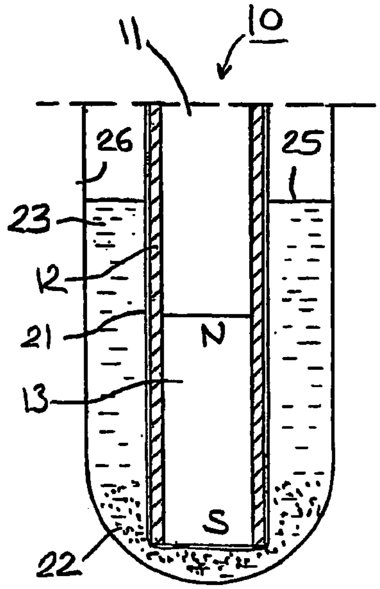

FIG. 7E presents the magnet unit 10 of FIG. 7D in a position where the ferromagnetic tube 12 has been moved to a position completely covering the magnet 13. The magnetic field is now eliminated and the micro-particles 22 are released into the liquid 23. This procedure is very well applicable for concentration into small liquid volumes.

FIGS. 8A-8E illustrate different steps of a process of collecting micro-particles 22 by means of a magnet unit 10 provided with a stretchable protective coating 21 by moving either the magnet 13 or the ferromagnetic tube 12. The magnet 13 is transversely magnetized.

Figure 8A:
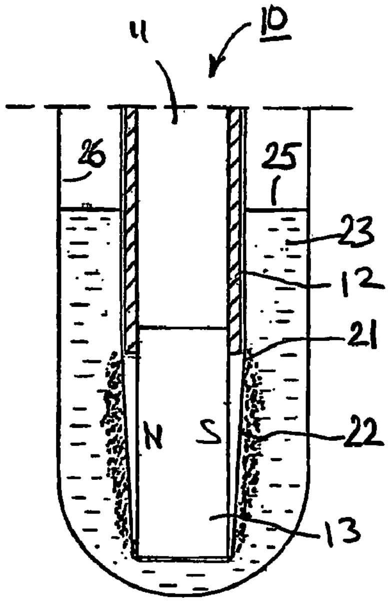
FIG. 8A-8E present embodiments of a magnet unit provided with a stretchable protective coating and a transversely magnetized magnet, placed in a solution.

FIG. 8A presents a magnet unit 10 in which a transversely magnetized magnet 13 has been pushed out from the ferromagnetic tube 12 so that it simultaneously stretches the stretchable protective coating 21. The micro-particles 22 now gather around the stretched protective coating 21 over a very large area.

Figure 8B:
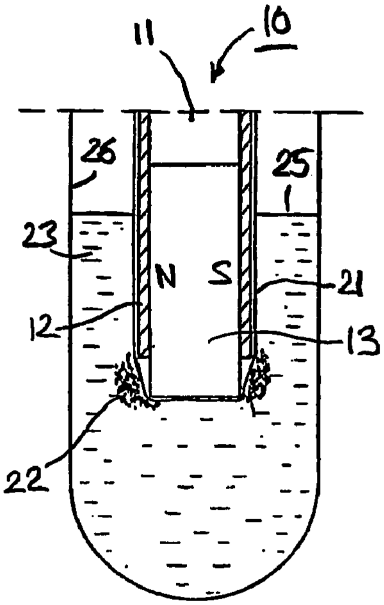

FIG. 8B presents the magnet unit 10 of FIG. 8A in a position where the magnet 13 has been moved upwards into the ferromagnetic tube 12. When the magnet 13 is moved upwards, the stretched protective coating 21 is restored to its original form, i.e. it moves upwards with the magnet 13. The micro-particles 22 move along with it and the whole micro-particle mass can be concentrated in a small area at the tip part of the protective coating 21.

Figure 8C:
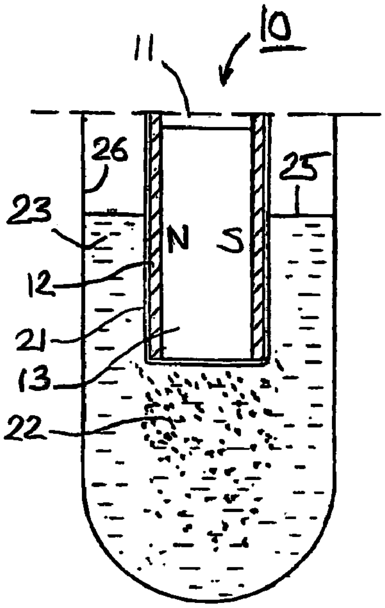

FIG. 8C presents the magnet unit 10 of FIG. 8B in a position where the magnet 13 has been completely retracted into the ferromagnetic tube 12. The micro-particles 22 are now released from the magnetic field into the solution 23.

Figure 8D:
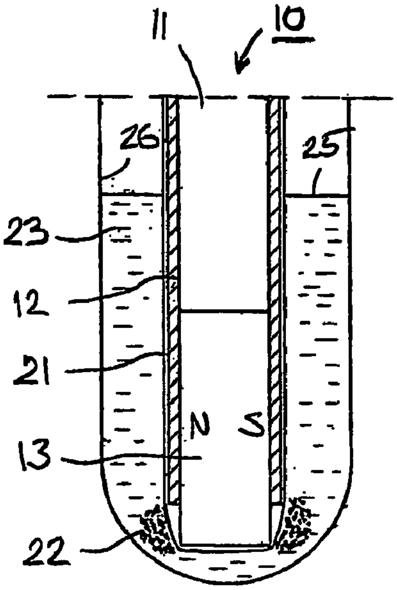

FIG. 8D presents the magnet unit 10 of FIG. 8A in a position where the ferromagnetic tube 12 has been moved downwards over the magnet 13. In this case, as in FIGS. 8B and 8C, micro-particles 22 can be collected from a large sample volume and concentrated in a small area at the tip part of the protective coating.

Figure 8E:
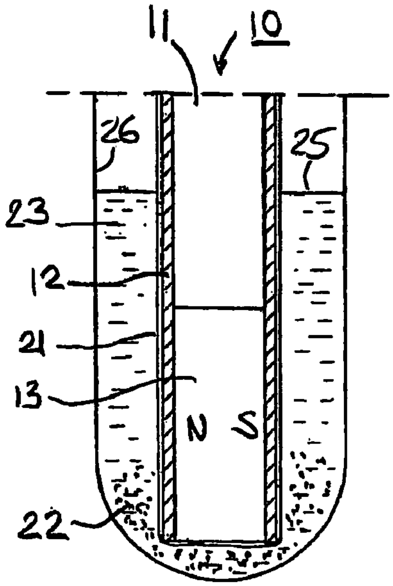

FIG. 8E presents the magnet unit 10 of FIG. 8D in a position where the ferromagnetic tube 12 has been moved to a position completely covering the magnet 13. The magnetic field is now eliminated and the micro-particles 22 are released from the magnetic field into the solution 23.

FIGS. 9A-9G illustrate different steps of a method of using a magnet unit 10 to collect a large mass of micro-particles 22 from large liquid volume and to concentrate them in to a small liquid volume.

Figure 9A:
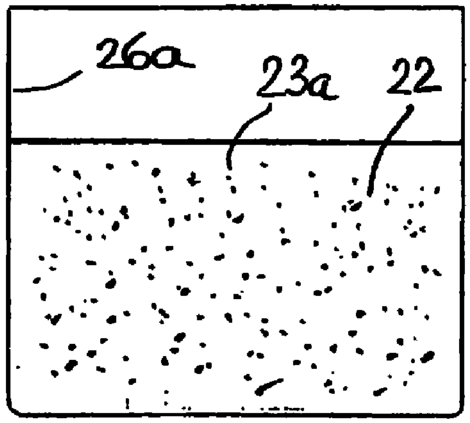
FIG. 9A-9G illustrate different stages of the use of the magnet unit when micro-particles are transferred from one vessel into another.

FIG. 9A presents a vessel 26*a* containing liquid 23 which contains micro-particles 22 are in large volume.

Figure 9B:
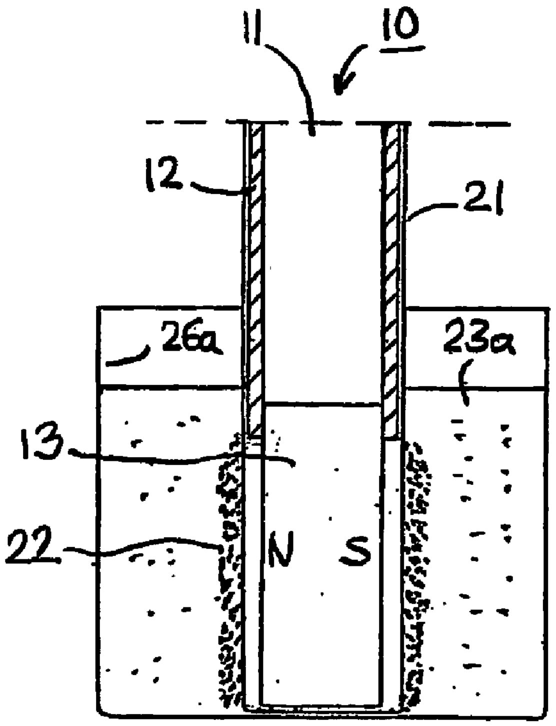

FIG. 9B presents a magnet unit 10 according to the invention placed in the vessel 26 shown in FIG. 9A. By means of the magnet unit 10, the micro-particles 22 are transferred from the solution 23*a* onto the surface of the protective coating 21 of the magnet unit 10. The magnet unit 10 in FIG. 9B comprises a magnet 13 protected with a non-stretchable protective coating 21 and magnetized in the transverse direction. Using such a magnet unit 10, the micro-particles 22 can be gathered in a large area on the surface of the protective coating 21.

Figure 9C:
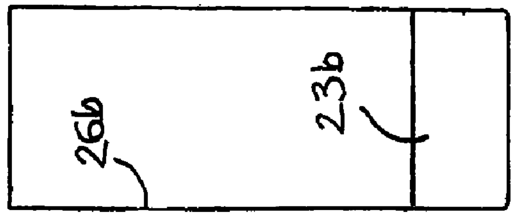

FIG. 9C presents another vessel 26*b*, which contains a small volume of liquid 23*b*. Into this vessel 26*b* are moved the micro-particles 22 collected by means of the magnet unit 10 from the vessel 26*a* in FIG. 9A. The vessel 26*b* presented in FIG. 9C has been so selected with respect to its dimensions and liquid capacity that it is suited for use with the magnet unit 10 presented.

Figure 9D:
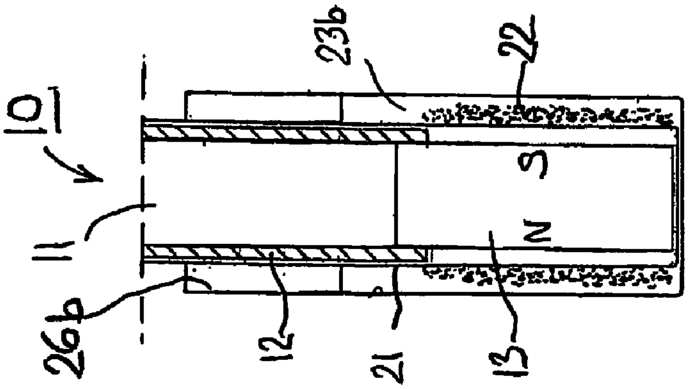
Figure 9E:
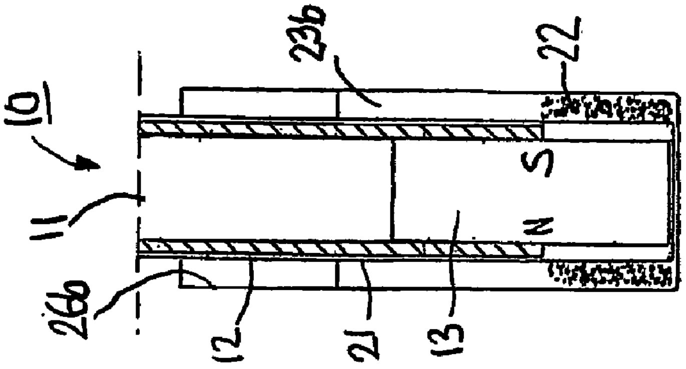
Figure 9F:
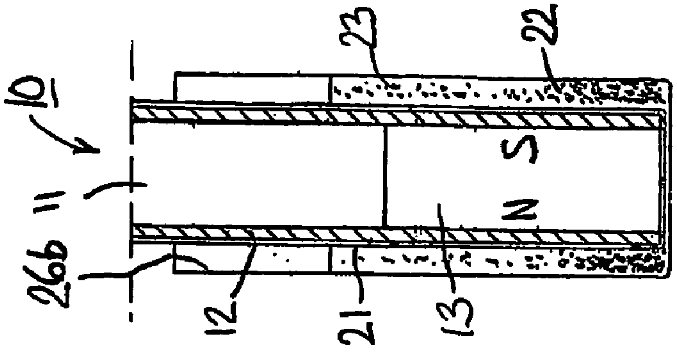

FIGS. 9D-9F illustrate different steps of a process of releasing micro-particles 22 collected from a large volume into a small volume.

FIG. 9D presents the magnet unit 10 immersed in the vessel 26*b*. Now the objective has been reached according to which, when the magnet unit 10 is immersed in the liquid 23*b*, the liquid level of the small liquid volume can be suitably raised over the limit up to which micro-particles 22 have been collected from the large vessel 26*a* presented in FIG. 9B. This method utilizes the circumstance that an object immersed in liquid displaces an amount of liquid equal to its own volume. When a vessel of a suitable design and shape and a magnet unit matched to it are used, the liquid surface in the vessel will rise to exactly the desired level. It is essential that the particles remain below the liquid surface.

FIG. 9E presents the magnet unit 10 of FIG. 9D in a situation where the ferromagnetic tube 12 is moved downwards. The micro-particles 22 are now released from the surface of the protective coating 21 from its upper part downwards.

FIG. 9F presents the magnet unit 10 of FIG. 9E in the following situation where the ferromagnetic tube 12 has been moved to a position completely covering the magnet 13 and no magnetic field remains outside the tube 12 to keep the micro-particles 22 on the surface of the protective coating 21. The micro-particles 22 are now completely released into the surrounding liquid 23*b*.

Figure 9G:
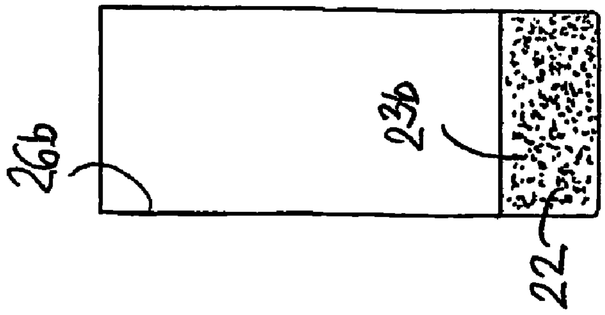

FIG. 9G illustrates a situation where the magnet unit 10 has been removed from the vessel 26*b* and the liquid surface has fallen back to its original level. As a final result of the operation, a large mass of micro-particles has been transferred into a small volume in an effective and simple manner, as illustrated in FIG. 9G. From this situation, the concentrating process can be continued in the manner described above or by using the methods illustrated in the preceding figures. Steps of transferring and concentrating micro-particles 22 can be performed in suitable different ways as necessary.

Figure 10:
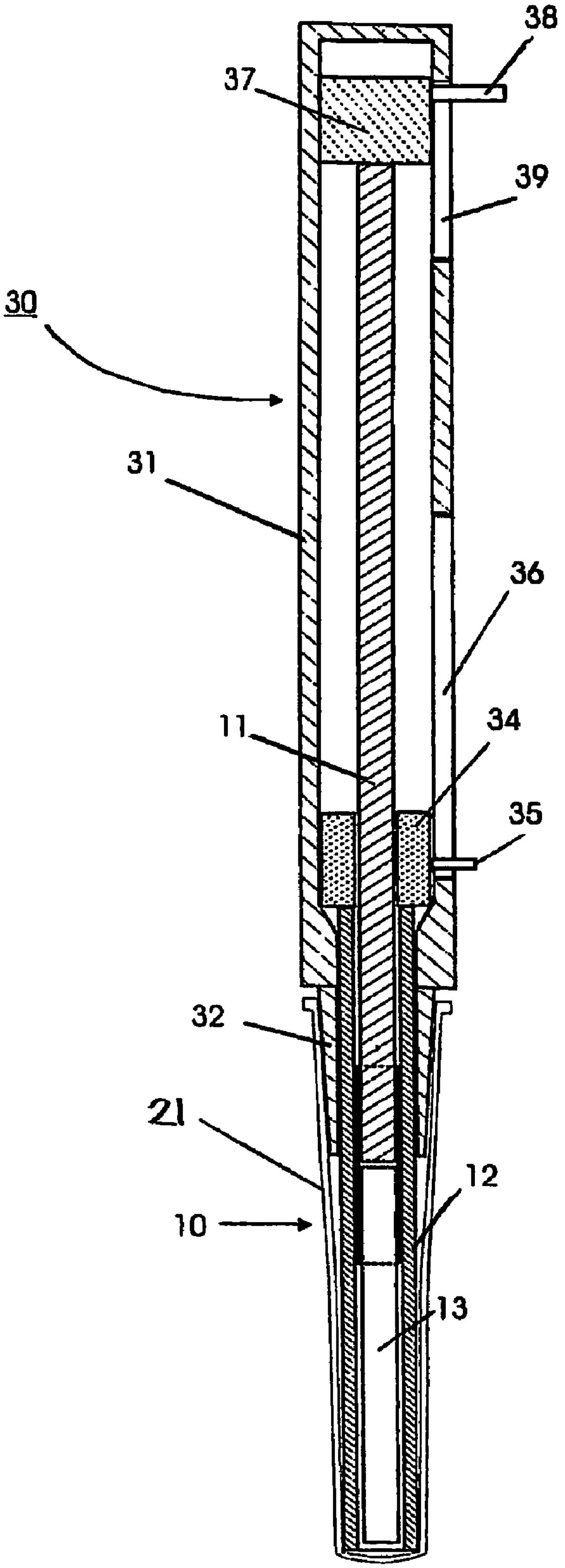
FIG. 10 presents a sectioned side view of a manually operated device for transferring micro-particles.

FIG. 10 presents an example of a manually operated transfer device 30 according to the invention for the transfer of micro-particles. The transfer device 30 comprises a frame tube 31, an adapter sleeve 32 forming an extension of the frame tube and a magnet unit 10 according to the invention at the end of the transfer device. The magnet unit 10 comprises a magnet 13, a bar or transfer rod 11, a ferromagnetic tube 12 and a stretchable or solid protective coating 21 pressed over the adapter sleeve 32.

The non-ferromagnetic rod 11 moving the magnet 13 of the magnet unit 10 extends to the upper part of the transfer device 30, where it is connected to a slide 37 for moving the magnet. This motion slide 37 is moved manually by means of a magnet moving pin 38 projecting out through the wall of the frame tube 31 from an elongated slot 39. The magnet moving pin 38 can be pushed upwards and downwards in the slot 39, thus causing the motion slide 37 and along with it the rod 11 and the magnet 13 to move upwards and downwards.

The micro-particle transfer device 30 further comprises a mechanism for moving the ferromagnetic tube 12 in the axial direction. This mechanism comprises a tube moving unit 34 and a tube moving pin 35, which also projects out through the frame tube 31 from a second elongated slot 36. The tube moving pin 35 can likewise be moved upwards and downwards in the slot 36, thus causing the tube moving unit 34 and therefore also the ferromagnetic tube 12 to move upwards and downwards.

The micro-particle transfer device 30 is held in the hand so that one can easily move both the magnet moving pin 38 and the tube moving pin 35 with a finger.

Figure 11:
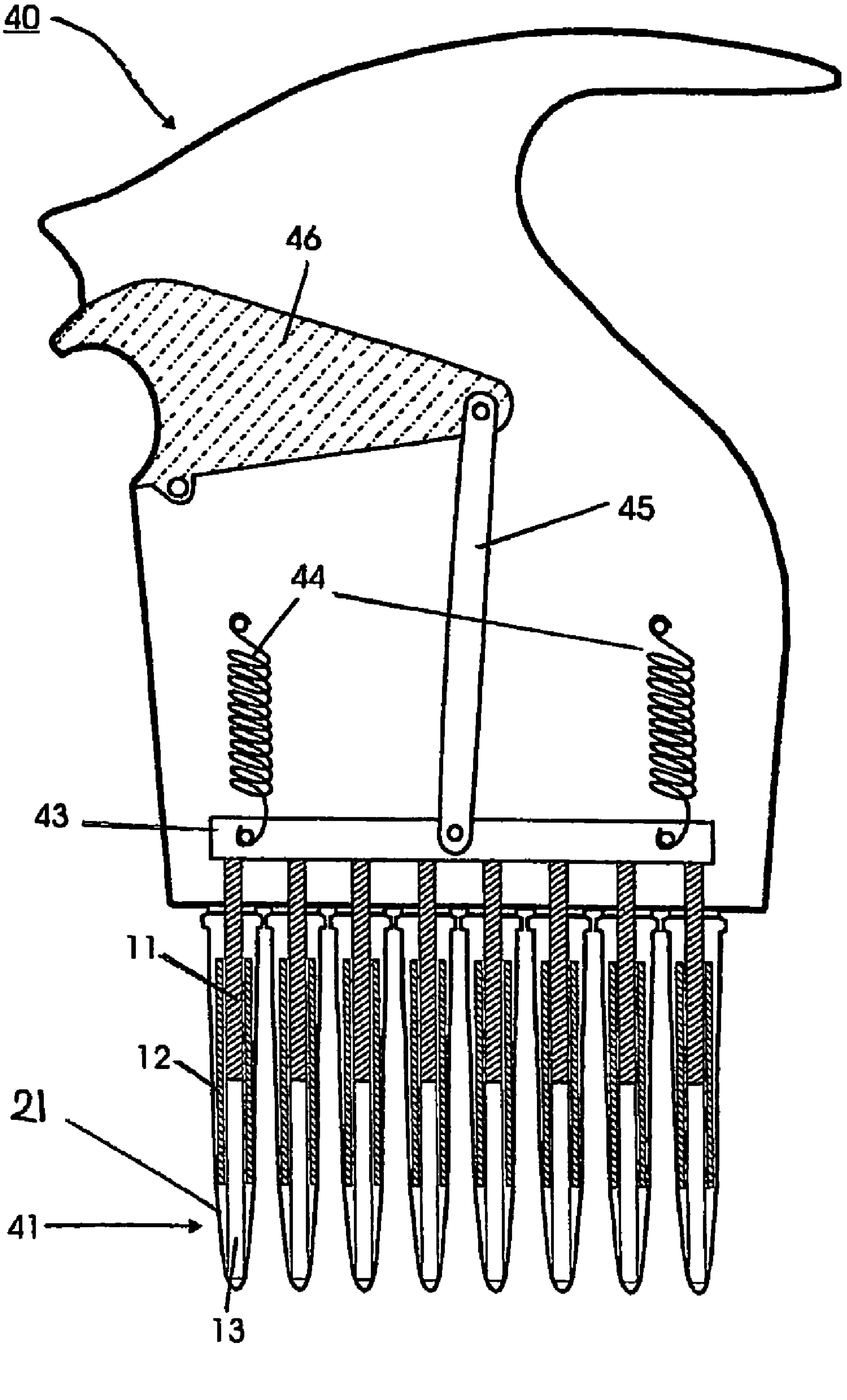
FIG. 11 presents a sectioned side view of a manually operated multi-channel device for transferring micro-particles.

FIG. 11 presents an example of a manually operated multi-channel micro-particle transfer device 40, which has a magnet unit array 41 consisting of eight magnet units 10 according to the invention. The magnet units 10 in the magnet unit array 41 are arranged in a row. Each magnet unit 10 comprises a magnet 13, a transfer rod 11, a ferromagnetic tube 12 and a protective coating 21. In the example presented in FIG. 11, the mechanism for moving the ferromagnetic tubes 12 upwards and downwards is not shown as in the previous example. The figure only presents by way of example a simple mechanism for moving all the eight magnets 13 of the magnet units 10 simultaneously.

In FIG. 11, the mechanism of the magnets 13 of the magnet units 10 comprises a tie bar 43, to which the rods 11 of all magnets 13 are connected. The magnets 13 of the multi-channel transfer device 40 are moved downwards and out of the ferromagnetic tubes 12 by pressing with a finger on a "trigger" 46 projecting partly outside the transfer device and connected by a connecting rod 45 to the tie bar 43 of the magnets 13. The magnets 13 are returned back to their upper position by means of return springs 44 connected to the tie bar 43.

According to an embodiment of the multi-channel transfer device 40, instead of moving all the magnets simultaneously, some of the magnets 13 can be locked in a desired position. In addition, different magnet units 10 may be provided with a mechanism allowing the ferromagnetic tubes to be moved upwards and downwards.

Figure 12:
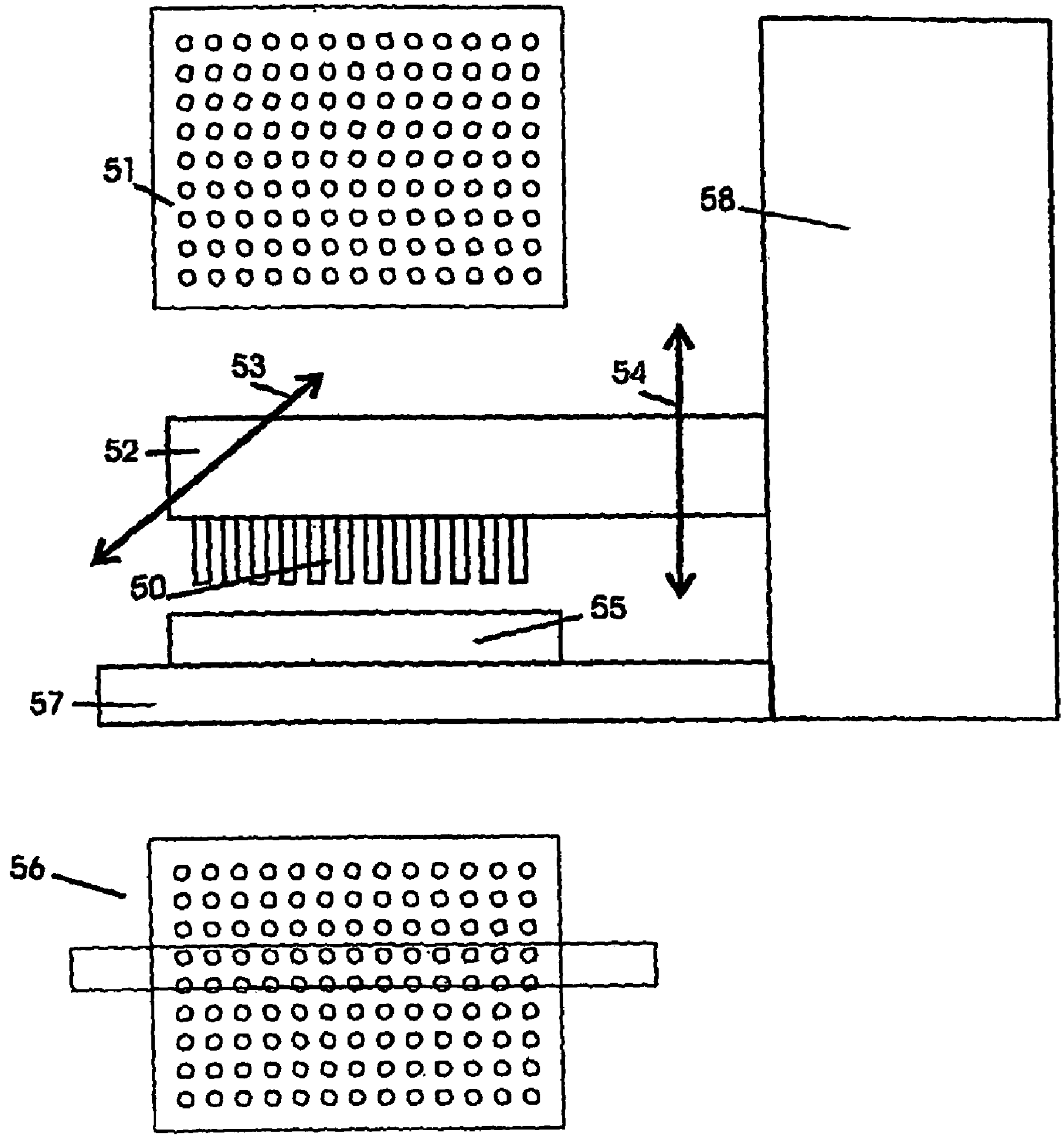
FIG. 12 presents a diagrammatic representation of an automated transfer device.

FIG. 12 presents an automatic micro-particle transfer device 50, which comprises magnet units according to the invention arranged in a row or in an n×m matrix 51 as illustrated in FIG. 12. The magnet units 10 are attached to a control unit 52, which contains the required mechanisms for moving the magnets and ferromagnetic tubes vertically. The control unit 52 itself can also move upwards and downwards in the direction indicated by arrow 54 and/or laterally as indicated by arrow 53. A sample plate 55 is placed on a support 57 under the magnet units either manually or by using a laboratory robot. The sample plate 55 has sample wells either in a single row or in a matrix 56 as shown in FIG. 12. The automatic device 50 further comprises a second control unit 58, which takes care of the motion logic system and contains all the necessary electronics for controlling the actuators of the automatic apparatus and managing the interactions with other laboratory equipment.

Figure 13:
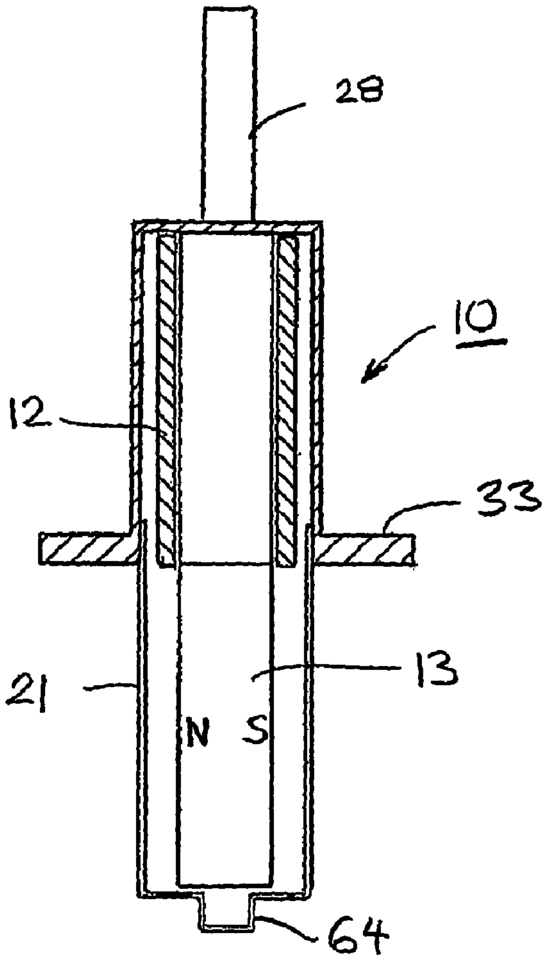
FIG. 13 presents a partially sectioned side view of yet another embodiment of the magnet unit.

FIG. 13 presents a magnet unit 10 according to the invention, which comprises a transversely magnetized magnet 13 and a ferro-alloy tube or sleeve 12 axially movable over the magnet 13. The magnet 13 is protected by a protective coating 21, which may be made of stretchable or hard material, preferably plastic or silicone rubber. In addition, the magnet unit 10 comprises a mounting flange 33 and a turning shaft 28, by means of which the magnet 13 inside the magnet unit 10 as well as the protective coating 21 can be rotated about their longitudinal axes.

Figure 14:
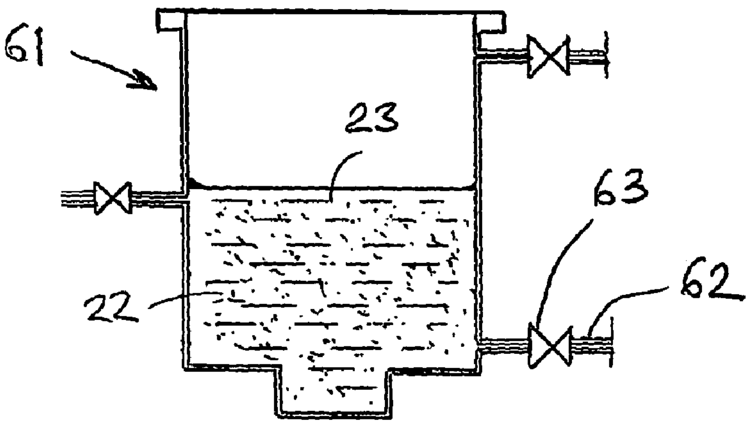
FIG. 14 presents a sectioned side view of a reactor vessel according to the invention.

FIG. 14 presents a reactor vessel 61 according to the invention with channels 62 provided with valves 63. The reactor vessel 61 contains an amount of liquid 23 needed in the process. The reactor vessel 61 and the magnet unit 10 presented in FIG. 13 together form a reactor unit 60 as illustrated in FIG. 15.

Figure 15:
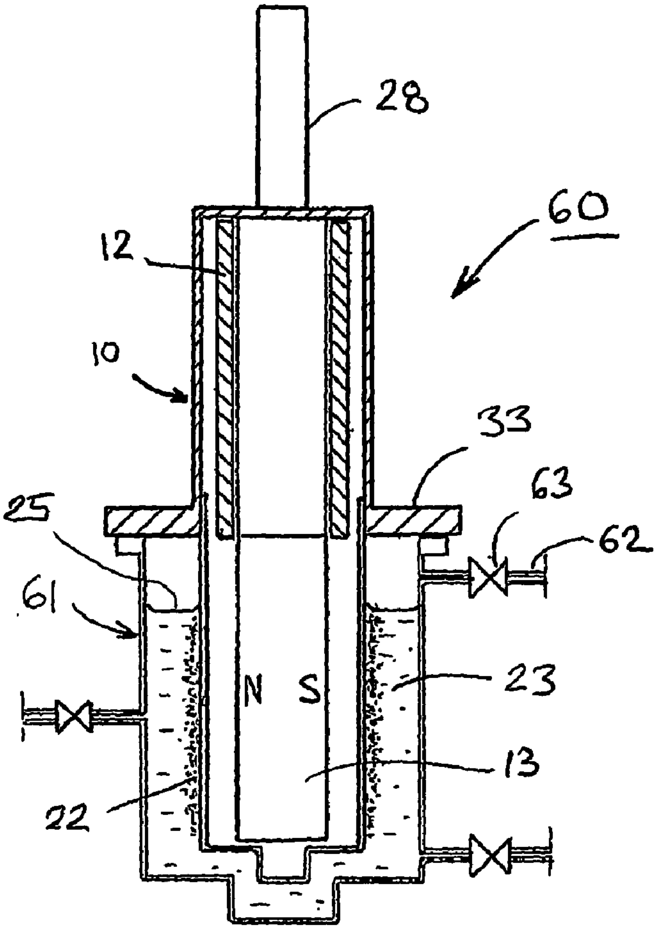
FIG. 15 presents a sectioned side view of a reactor unit according to the invention.

FIG. 15 presents a reactor unit 60 according to the invention, wherein the reactor vessel 61 contains the solution 23 needed in the process. The solution contains e.g. an incubation medium, a sample, a buffer solution and magnetic particles 22, such as micro-particles. The reactor vessel 61 is then connected to the mounting flange 33 of the magnet unit 10. It is still possible to introduce substances, such as suitable solutions and magnetic particles, into the reactor 60 according to need, or to remove liquids through the channels 62 connected to the reactor vessel and provided with valves 63. The channels 62 or corresponding inlets may be disposed at the sides or at the ends of the reactor vessel, and there may be several such inlets, which may be placed on different sides of the reactor unit. Via the channels 62, it is possible to control e.g. the gases inside the reactor unit 60, the pH-values and salt content. Through the inlet channels 62 it is also possible to introduce more sample into the reactor unit 60 and/or to extract sample from the reactor unit 60. These inlets may be provided with suitable filters, by means of which the gas or solution to be introduced can also be kept sterile. In FIG. 15, magnetic particles 22 have gathered on the surface of the protective coating 21.

Figure 16:
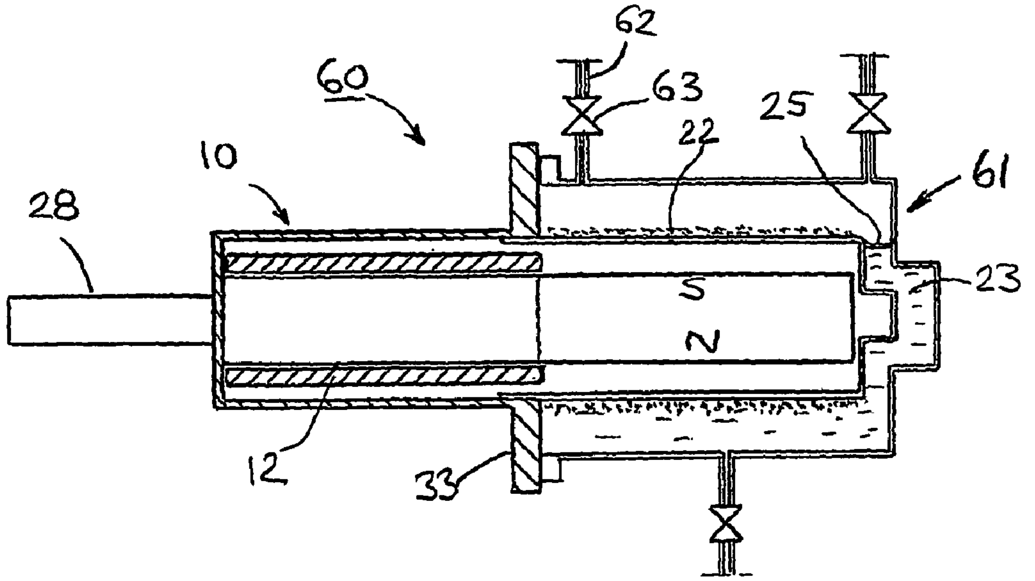
FIG. 16 presents the reactor unit of FIG. 15 in a horizontal position.

FIG. 16 presents the reactor unit 60 of FIG. 15 in a horizontal position. If the reactor unit 60 is held on its side in this position and the magnet 13 of the magnet unit 10 and the protective coating 21 are rotated in relation to the protective casing of the magnet unit 10, then the liquid 23 inside the reactor unit 60 will be efficiently mixed. Thus, the magnetic particles are also mixed in the liquid. The level of the liquid surface 25 in the reactor unit 60 can be adjusted and optimized according to the application being used.

To achieve more effective mixing of the liquid 23 inside the reactor unit 60, the protective coating 21 of the magnet 13 can be provided with suitable vanes. When the protective coating 21 and the vanes are being rotated, the liquid 23 in the reactor vessel 61 is set in motion and effectively mixed. Instead of using vanes, the surface of the protective coating 21 can also be shaped in different ways. The protective coating 21 can also be provided with a suitable shaping in its tip part 64, which will then support the magnet unit when the latter is in the horizontal position on its side.

In the process used, the magnetic particles may be already adhering to the protective coating 21 of the magnet 13 before the process or they may be caused to adhere to it during the process. According to the invention, the collection and release of the magnetic particles from the protective coating 21 are implemented by means of the ferromagnetic sleeve 12, which is moved longitudinally over the magnet 13 so as to cover or expose the magnet. In the embodiment described, the magnet 13 used is a transversely magnetized magnet. It is essential that the magnetic particles can be collected in the reactor unit 60 on a large surface around the protective coating 21.

As the magnetic particles adhere to the protective coating 21, there is a very large active area in the medium, allowing e.g. proteins, cells, DNA or bacteria to be collected from the solution 23 in the reactor vessel 61. By mixing the solution, the solution under treatment can be caused to flow past the magnetic particles adhering to the protective coating 21 so that the desired components will be caught on the magnetic particles. In the reactor unit 60 it is also possible to release the magnetic particles temporarily into the solution in the manner described in the invention and then pick the magnetic particles again from the solution onto the protective coating 21.

Figure 17:
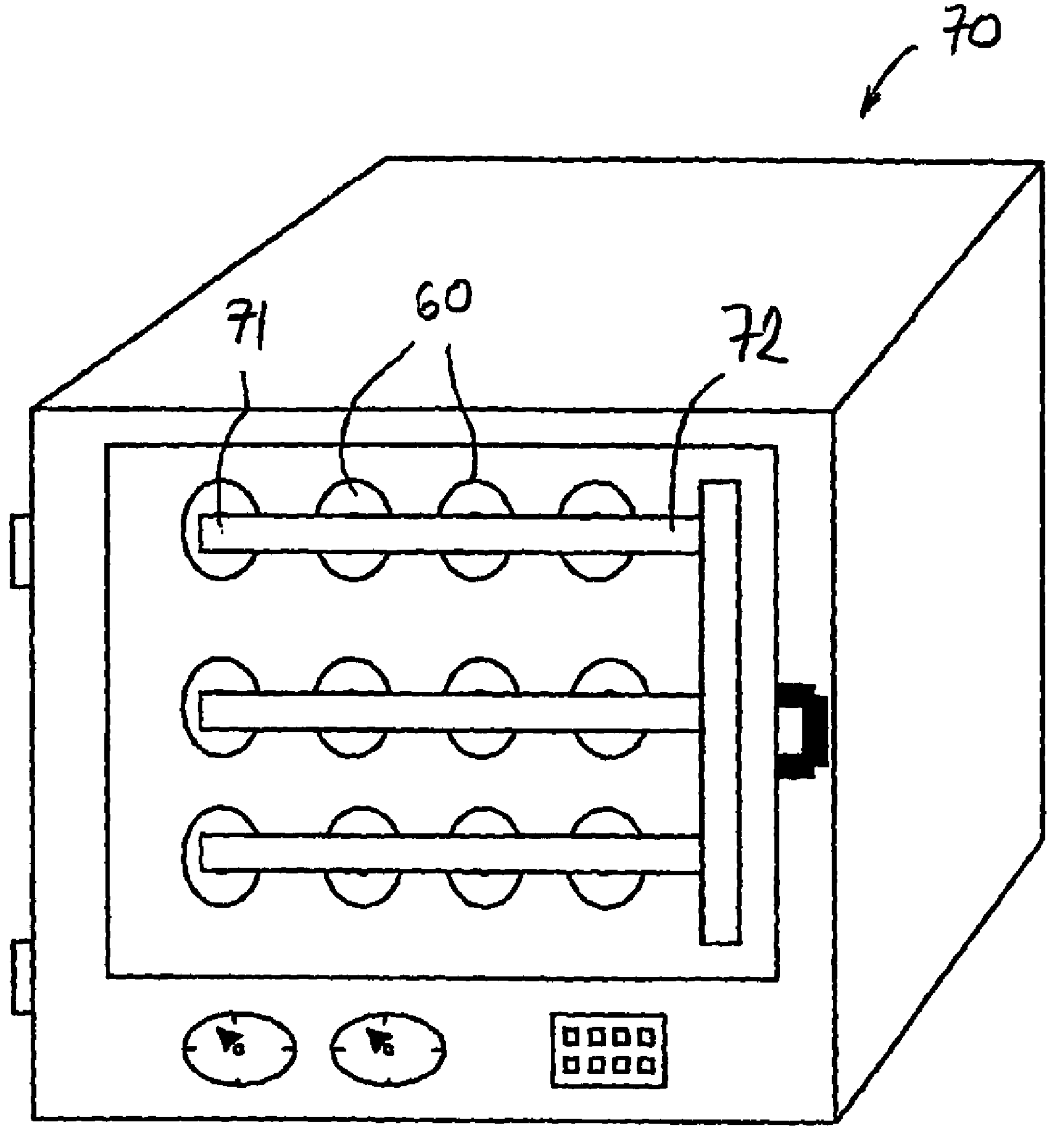
FIG. 17 presents a perspective view of an environmental cabinet according to the invention.

FIG. 17 presents an environmental cabinet 70 according to the invention, which can accommodate several reactor units 60 simultaneously. By means of a motor 71 and an actuator 72 connected to the environmental cabinet 70, it is possible to rotate the magnets 13 and protective coatings 21 in several reactor units 60 at the same time. In the environmental cabinet 70, it is possible to control e.g. the temperature, the speed of rotation of the magnets and their protective coatings, the exchange of gases inside the reactor units, the sampling from the reactor units and the additions of solutions into the reactor units.

Such a solution is particularly useful in microbiological quality control, where the reactor units 60 can be used to incubate e.g. pathogenic bacteria. Upon the lapse of a suitable length of time, the reactor units 60 are removed from the environmental cabinet 70. In the magnet units 10, the magnetic particles are now collected on the surface of the protective coating 21. The magnet unit 10 of the reactor 60 is released from the reactor vessel 61, whereupon the magnetic particles can be e.g. washed and concentrated in separate containers. Everything else except the magnetic particles is left in the reactor vessel 61. The apparatus is capable of treating very large liquid volumes.

Figure 18:
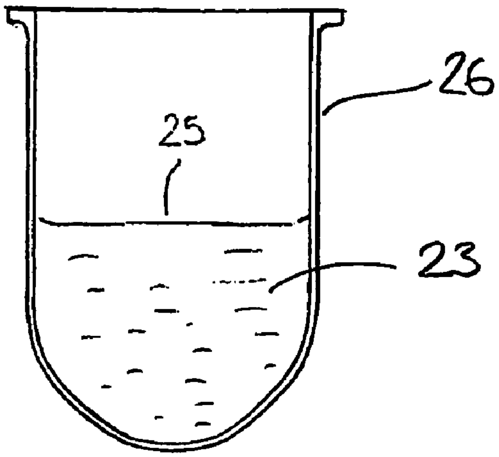
FIG. 18 presents a tube in sectioned side view.
Figure 19:
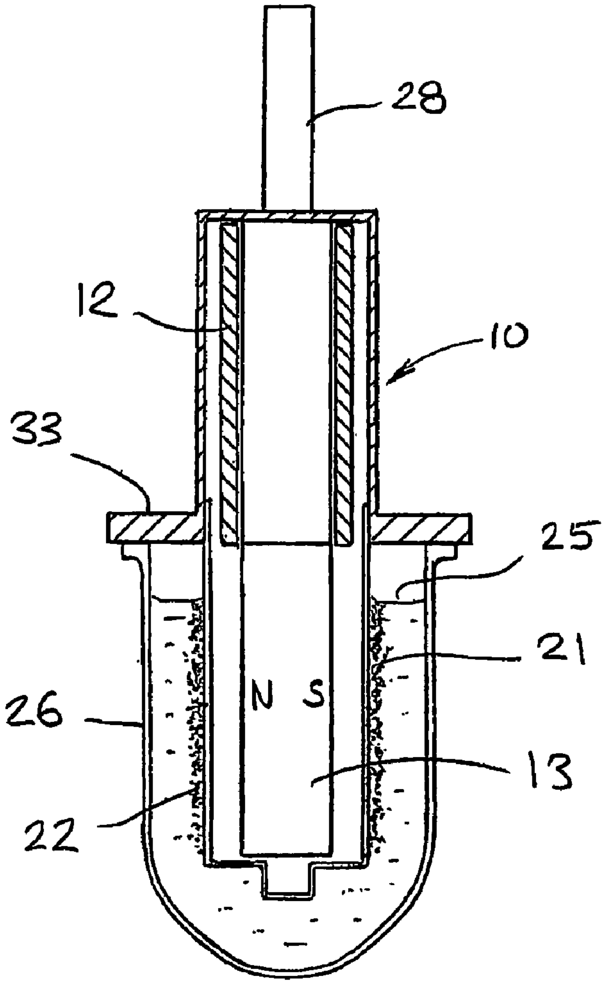
FIG. 19 presents a sectioned side view of a tube in conjunction with a magnet unit with the sleeve in a first position.

FIG. 18 presents a test tube 26 containing an amount of suitable liquid, such as washing liquid. The magnet unit 10 detached from the reactor 60 is introduced into the test tube 26 as shown in FIG. 19. At this stage, the magnetic particles 22 still remain gathered on the protective coating 21. In this situation, the liquid surface 25 of the solution 23 has to be above the area of adherence of the magnetic particles 22 on the surface of the protective coating 21 so that the magnetic particles 22 remain below the liquid surface 25.

Figure 20:
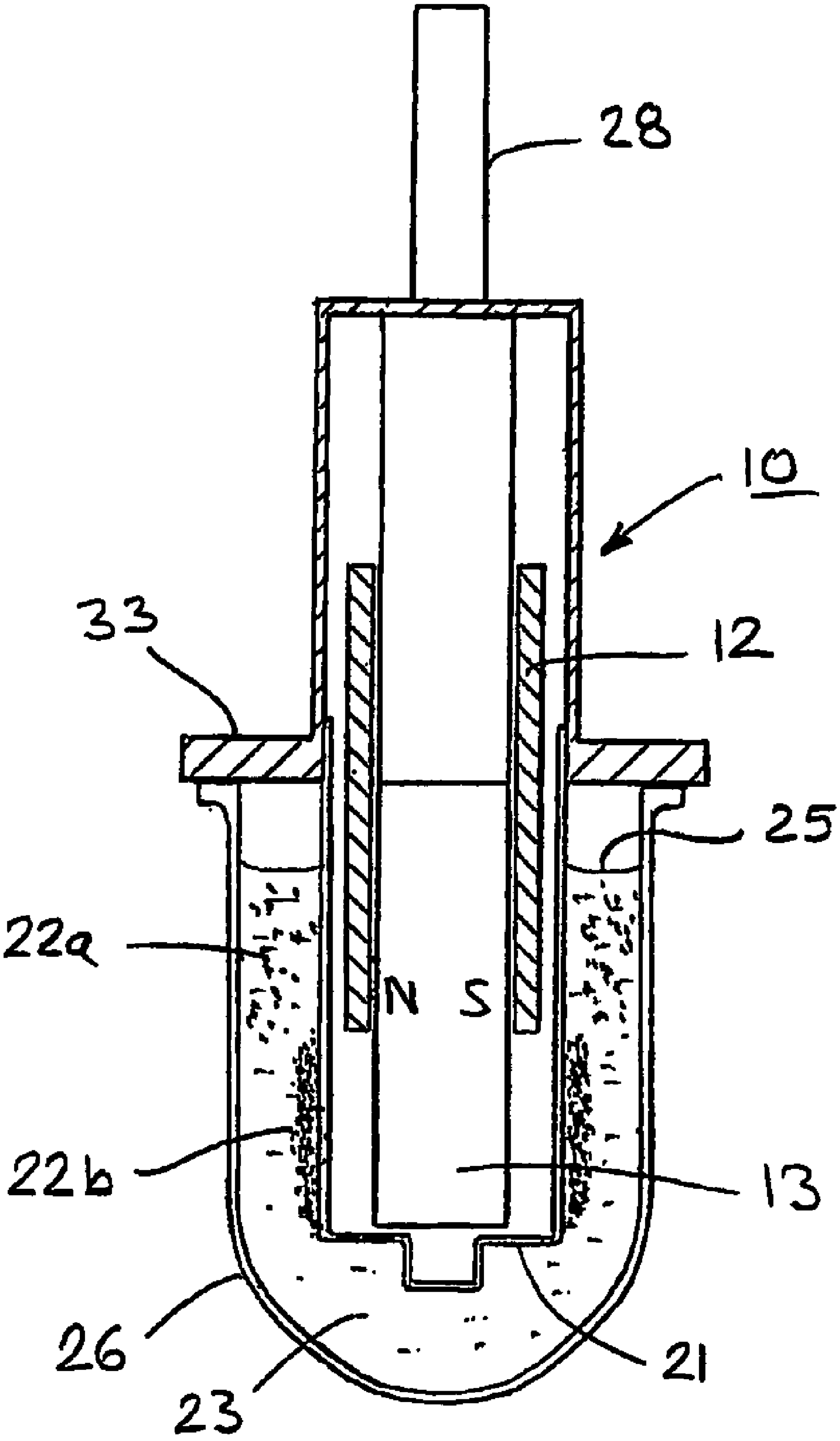
FIG. 20 corresponds to FIG. 19 and illustrates a situation where the sleeve of the magnet unit is in a second position.

FIG. 20 shows a situation where the ferromagnetic sleeve 12 of the magnet unit 10 is being moved downwards in the figure. It can be seen from FIG. 20 that the ferromagnetic sleeve 12 is already in a position partially covering the magnet 13. As a result of the ferromagnetic sleeve 12 being slid over the magnet 13, the magnetic field disappears from the area covered, and thus part of the magnetic particles 22*a* are released from the surface of the protective coating 21 starting from above. Where the ferromagnetic sleeve 12 does not yet cover the magnet 13, the magnetic field still holds the rest of the magnetic particles 22*b* on the surface of the protective coating 21.

Figure 21:
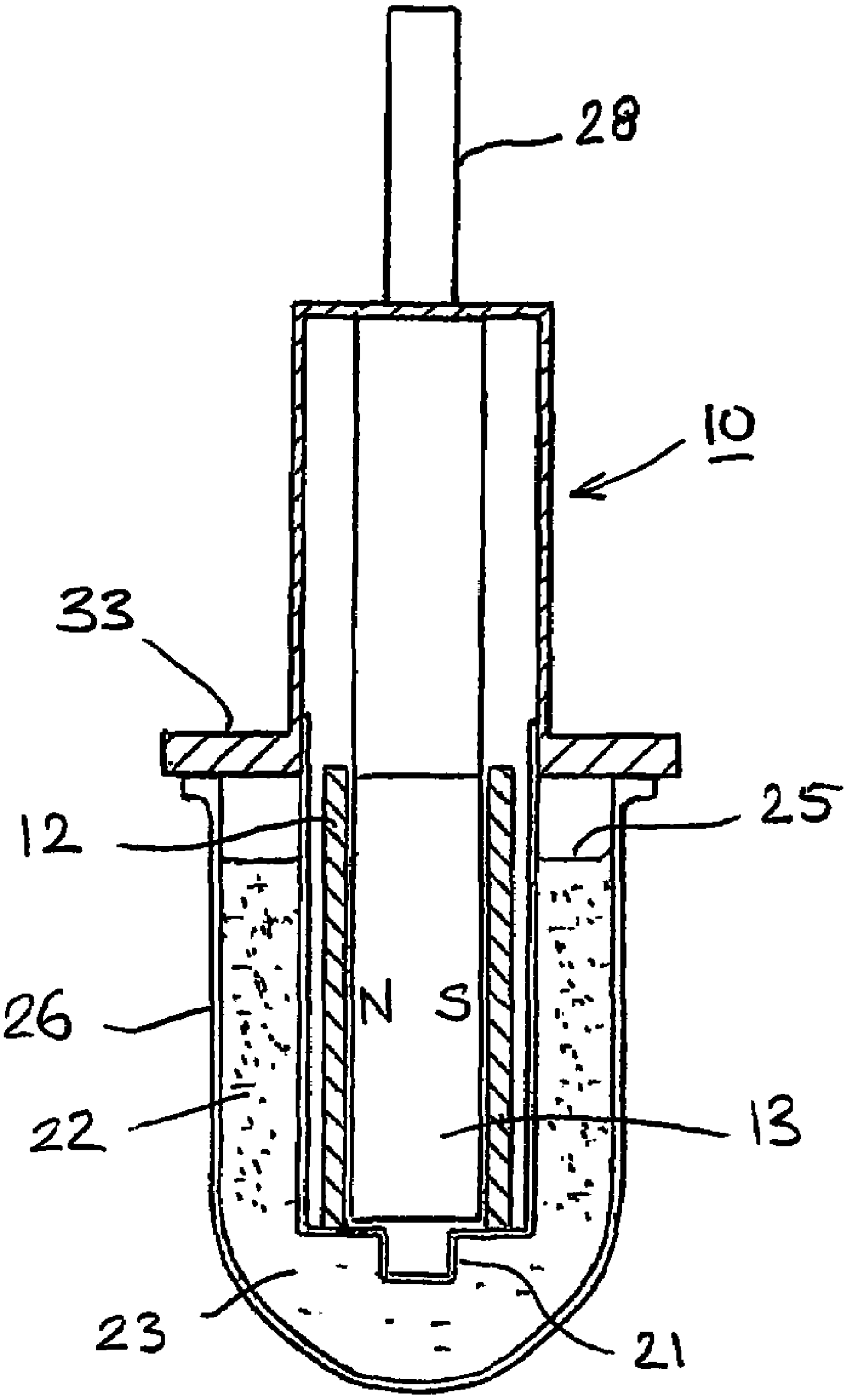
FIG. 21 corresponds to FIG. 19 and illustrates a situation where the sleeve of the magnet unit is in a third position.

In FIG. 21, the ferromagnetic sleeve 12 has moved to a position completely covering the magnet 13. The ferromagnetic sleeve 12 has thus caused a complete disappearance of the magnetic field, with the result that that all the magnetic particles 22 have been released from the surface of the protective coating 21 into the solution 23.

In FIG. 22, the magnet unit 10 has been removed from the test tube 26, the magnetic particles 22 and the components bound thereto, such as e.g. bacteria, being thus concentrated in the test tube separated from the reactor unit 60. Using the same magnet unit 10, it is now possible to continue processing the sample in smaller volumes by limiting the binding area of magnetic particles 22 by means of the ferromagnetic sleeve 12 to the extreme tip part of the protective coating 21. The magnetic particles 22 can be collected from the test tube 26 and transferred into the next test tubes and, and they can be e.g. washed in required quantities.

It is also possible to isolate the DNA, RNA, protein or surface antigen of the bacteria collected from the reactor unit 60 using reagents specifically intended for them. The bacteria generally have to be digested by means of different devices and/or reagents before further analyses. After the digestion, the next magnetic particles having different binding properties can be added to the bacteriolysate thus obtained. Using magnetic particles having a new property, e.g. the desired bacterial protein, antigen, DNA, rNA, RNA or mRNA is collected from the bacteriolysate. In the reactor unit 60, the magnetic particles 22 intended for the collection of bacteria may have been removed before magnetic particles having new properties are introduced into the process.

Using the method described in the invention, components as mentioned above can be isolated, washed and released for an actual analysis. As analyzing methods, it is possible to use e.g. PCR amplification or ELISA assay. In a reactor vessel 61 like the one described, it is possible to incubate both aerobic and anaerobic micro-organisms.

Figure 23:
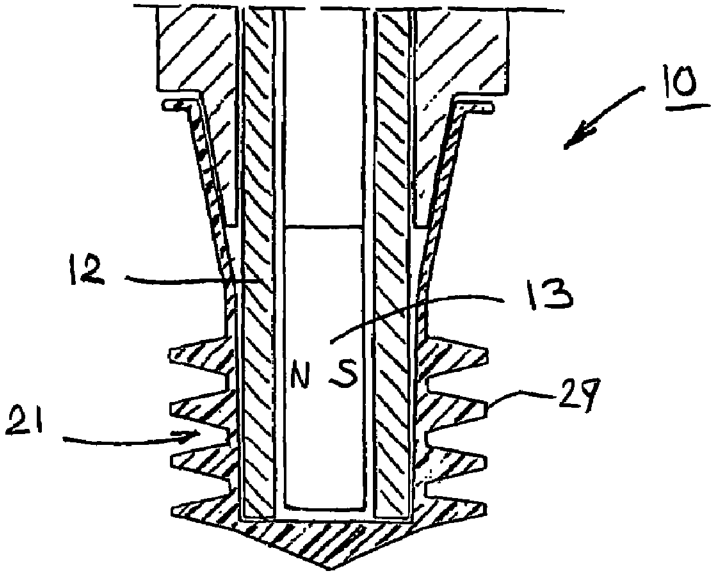
FIG. 23 presents a partially sectioned side view of an embodiment of the magnet unit provided with a different protective coating.

FIG. 23 presents a magnet unit 10 comprising a transversely magnetized magnet 13, a ferromagnetic sleeve 12 and a protective coating 21 having ridges 29 in its outer surface. Between the ridges 29 there are recesses where micro-particles 22 will gather which ensure both that a large quantity of micro-particles can be reliably collected on a large surface and that they can be transferred from one vessel into another.

Figure 24:
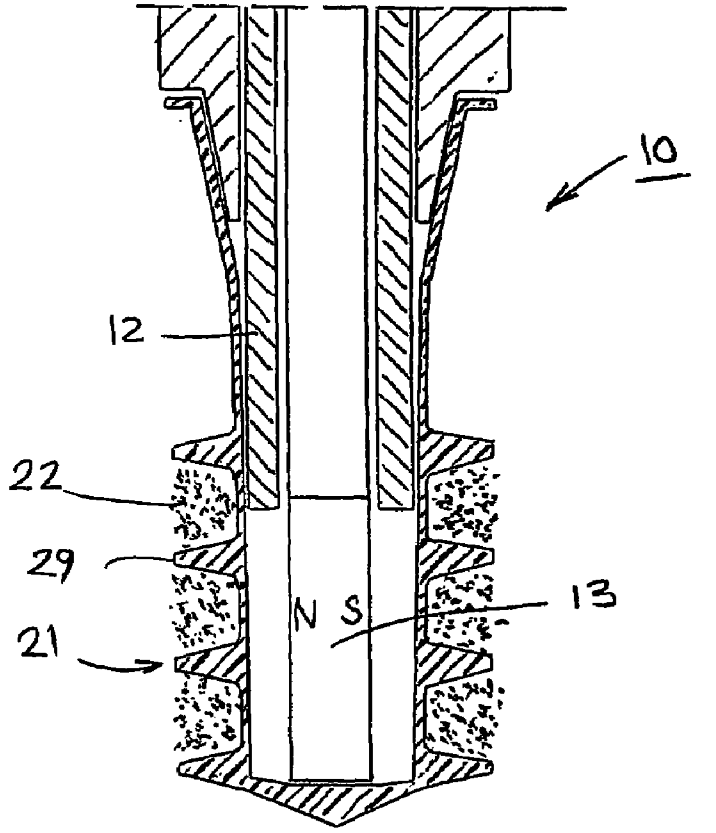
FIG. 24 corresponds to FIG. 23 and illustrates the operation of the magnet unit during a second stage.

FIG. 24 presents the magnet unit 10 of FIG. 23 in a position where the magnet 13 has been pushed out completely from the ferromagnetic sleeve 12. The transversely magnetized magnet 13 now gathers micro-particles 22 on the protective coating 21 over the entire length of the magnet. When the magnet 13 is being pushed out, the protective coating 21 is simultaneously stretched so that large recesses or pockets are formed between the ridges 29. The micro-particles 22 are caught in these pockets so that they are easily held in place when the magnet unit 10 is lifted up. The micro-particles 22 will not be released from the pockets by the liquid flow resulting from the movement of the magnet unit 10 or by the disturbing effect of the liquid tension caused by the penetration of the surface.

Figure 25:
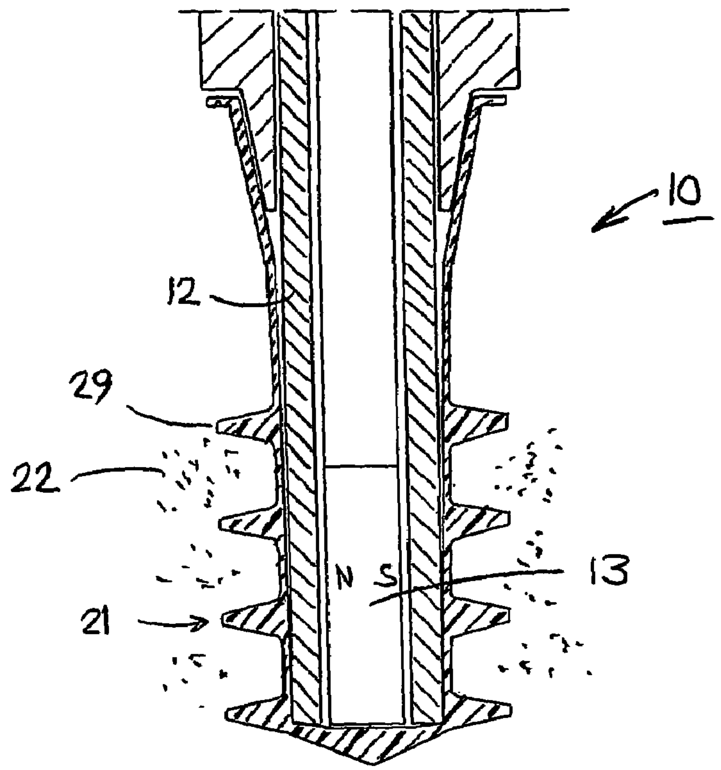
FIG. 25 corresponds to FIG. 23 and illustrates the operation of the magnet unit during a third stage.

FIG. 25 illustrates a situation where the magnet 13 has been pushed out completely from the ferromagnetic sleeve 12 and at the same time the ferromagnetic sleeve 12 is also pushed out completely. The ferromagnetic sleeve 12 surrounding the magnet 13 now cancels the magnetic force of the magnet 13 and the micro-particles 22 are released from the protective coating and dispersed back into the liquid.

Figure 26:
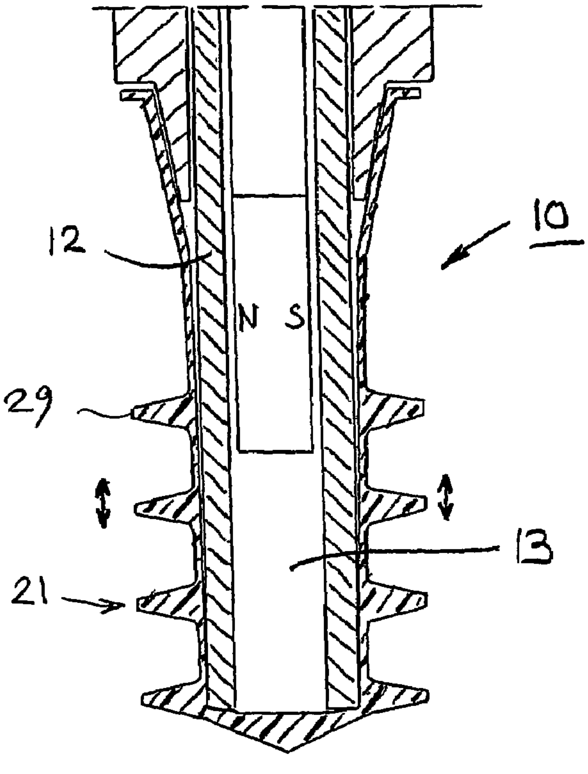
FIG. 26 corresponds to FIG. 23 illustrates the operation of the magnet unit during a fourth stage.

FIG. 26 again illustrates a situation where only the ferromagnetic sleeve 12 has been pushed out completely. In this case, too, the magnet 13 has no magnetic force, and consequently the micro-particles 22 do not gather on the protective coating 21. Instead, this stage illustrated by FIG. 26 can be used alternately with the stage illustrated by FIG. 23, thus producing in the liquid a pumping effect causing efficient mixing. Naturally, the stages illustrated in FIGS. 24 and 25 can also be used alternately, in other words, when the magnet 13 has been pushed out completely, only the ferromagnetic sleeve 12 is moved back and forth. This also produces in the liquid a pumping and mixing effect.

Figure 27:
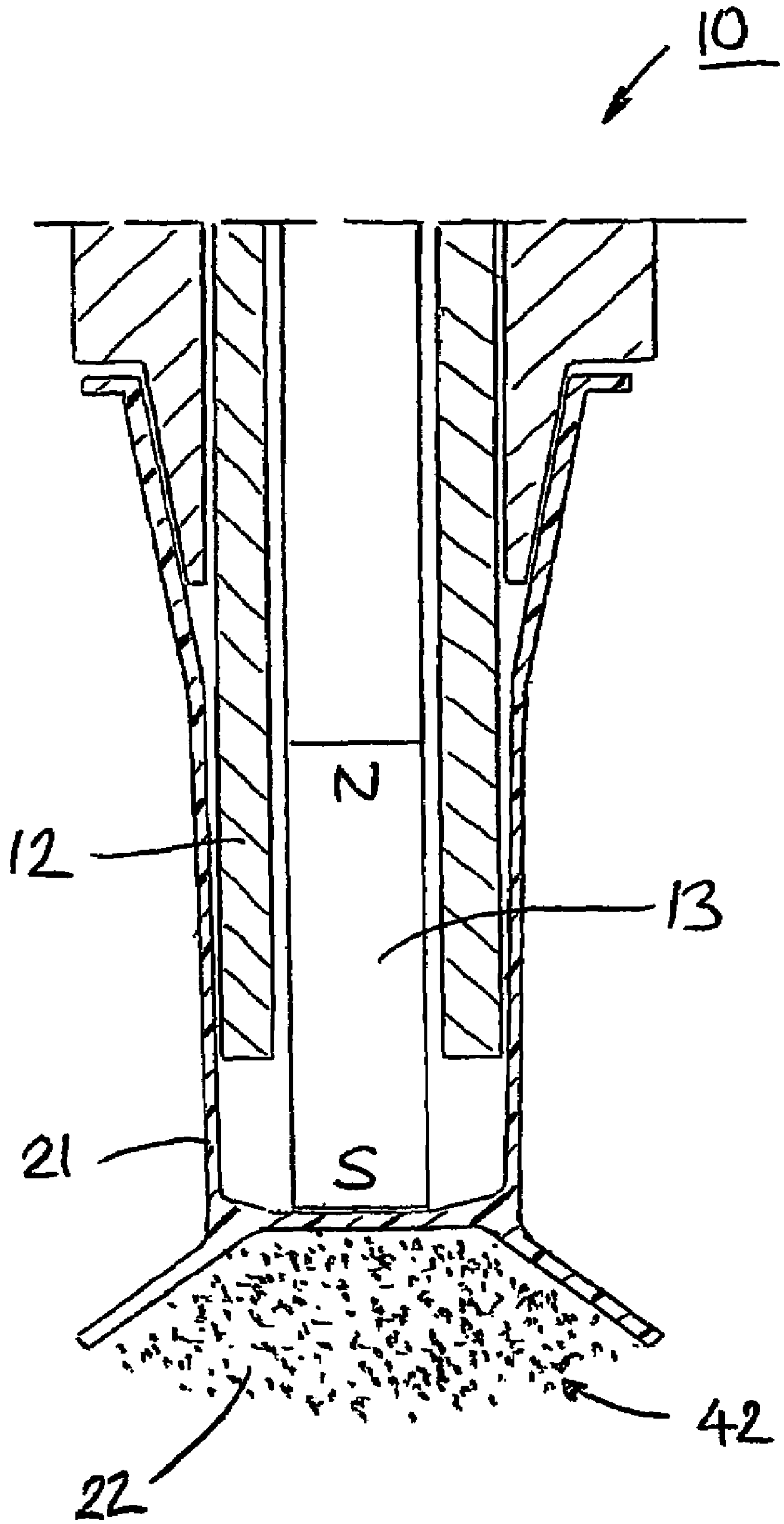
FIG. 27 presents a partially sectioned side view of yet another embodiment of the magnet unit provided with a different protective coating.

FIG. 27 presents a magnet unit 10 comprising a longitudinally magnetized magnet 13, a ferromagnetic sleeve 12 and a protective coating 21 provided with a pocket 42 for micro-particles 22. With such a structure, it is also possible to collect a large quantity of micro-particles 22 which will not be easily released from the surface of the protective coating 21 during the transfer.

Figure 28:
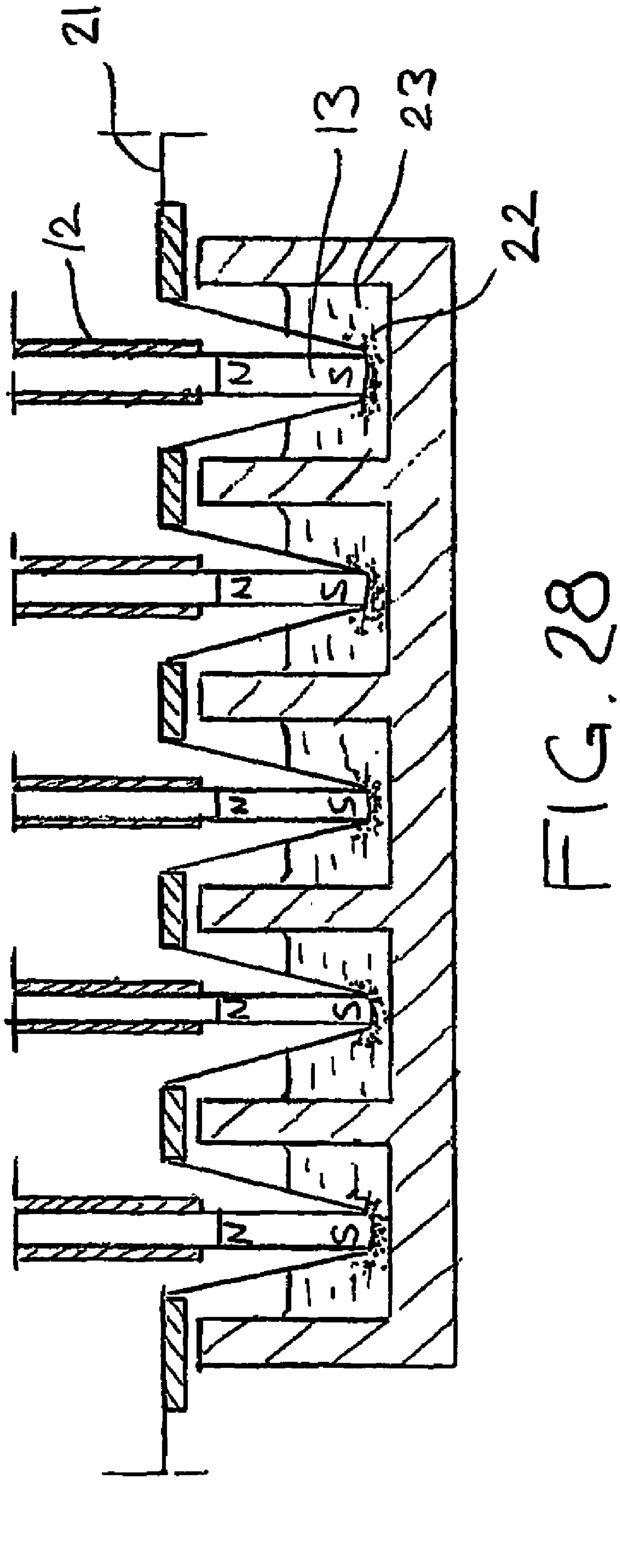
FIG. 28 presents a diagrammatic and sectioned side view of a number of parallel magnet units having a common sheet-like protective coating.

FIG. 28 presents a number of parallel magnet units 10 having a common sheet-like protective coating 21. The protective coating 21 is made of stretchable material, allowing the same coating to be used in common by adjacent magnet units 10. The coating is preferably taken from a roll, in which case it can also be easily changed.

Figure 29:
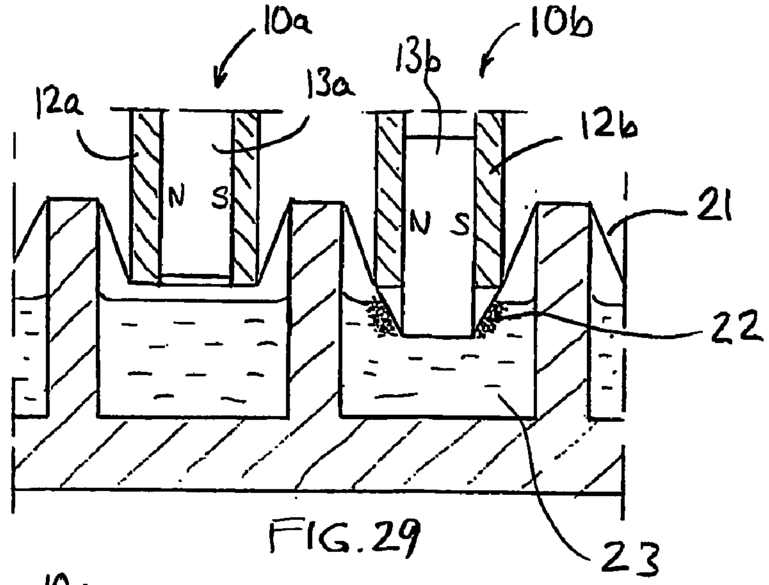
FIG. 29 corresponds to FIG. 28 and presents parallel magnet units according to another embodiment.

FIG. 29 presents two parallel magnet units 10*a* and 10*b*, which have a common protective coating 21. In the device presented in FIG. 29 as an example, the magnet units 10*a* and 10*b* operate out of phase. The ferro-alloy sleeves 12*a* and 12*b* of each magnet unit 10*a* and 10*b* are pressed against the protective coating 21 so that the protective coating 21 is pressed against the edges of the wells in the microplate, thus closing and sealing the wells. The magnet of magnet unit 10*b* has additionally been pushed downwards towards the microplate well so that the protective coating 21 and the end of magnet 13 13*b* inside it are in the liquid 23. The microparticles 22 in the liquid 23 now gather on the surface of the protective coating 21 at the end of the transversely magnetized magnet 13*b*.

Figure 30:
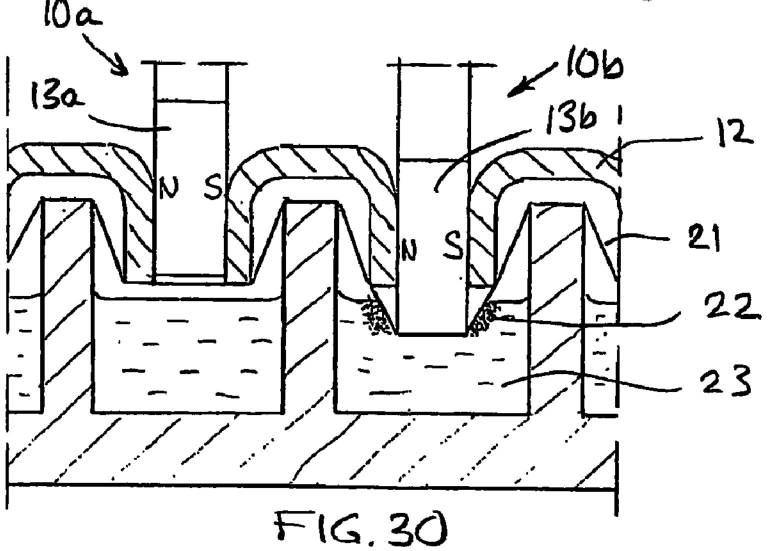
FIG. 30 corresponds to FIG. 28 and presents parallel magnet units according to a third embodiment.

FIG. 30 presents an embodiment in which the magnet units 10*a* and 10*b* have no separate ferro-alloy sleeves. These have been replaced by a ferro-alloy plate 12, which has been so shaped that it has downwards pointing projections in alignment with the wells of the microplate. The magnets 13*a* and 13*b* are placed in apertures in the projections in the ferro-alloy plate 12. In FIG. 30, the magnets 13*a* and 13*b* of the magnet units 10 10*a* and 10*b* are out of phase in the same way as in FIG. 29.

Figure 31:
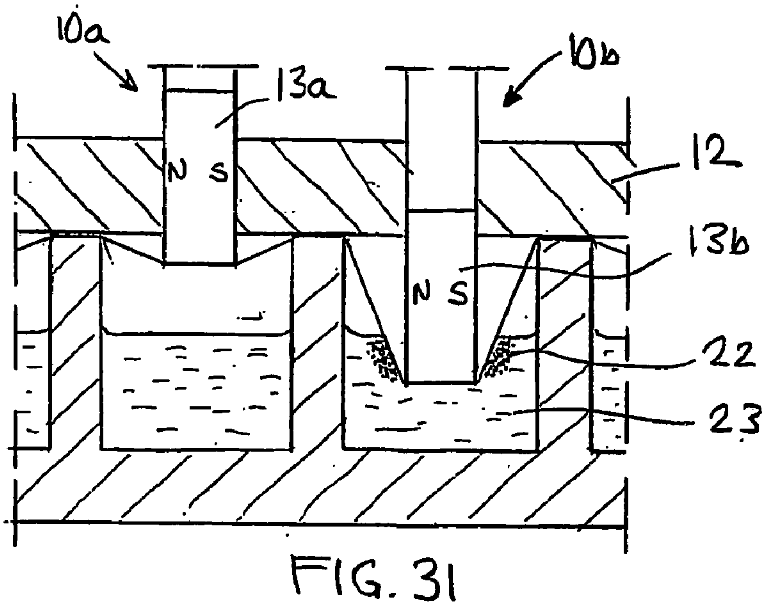
FIG. 31 corresponds to FIG. 28 and presents parallel magnet units according to a fourth embodiment.

FIG. 31 presents an embodiment in which the magnet units 10*a* and 10*b* also have a common ferro-alloy plate 12 in place of the sleeves, which in this case is a straight plate. The magnets 13*a* and 13*b* are placed in apertures in the ferro-alloy plate 12. In this figure, too, the magnets 13*a* and 13*b* of the magnet units 10*a* and 10*b* are out of phase. By difference from the solution illustrated by FIG. 29, the protective coating 21 is pressed against the edges of the microplate wells by means of the magnets 13*a* and 13*b* instead of ferromagnetic sleeves. The magnet 13*a* of magnet unit 10*a* is in a sealing position whereas the magnet 13*b* of the other magnet unit 10*b* is in a position for collecting micro-particles 22.

Figure 32:
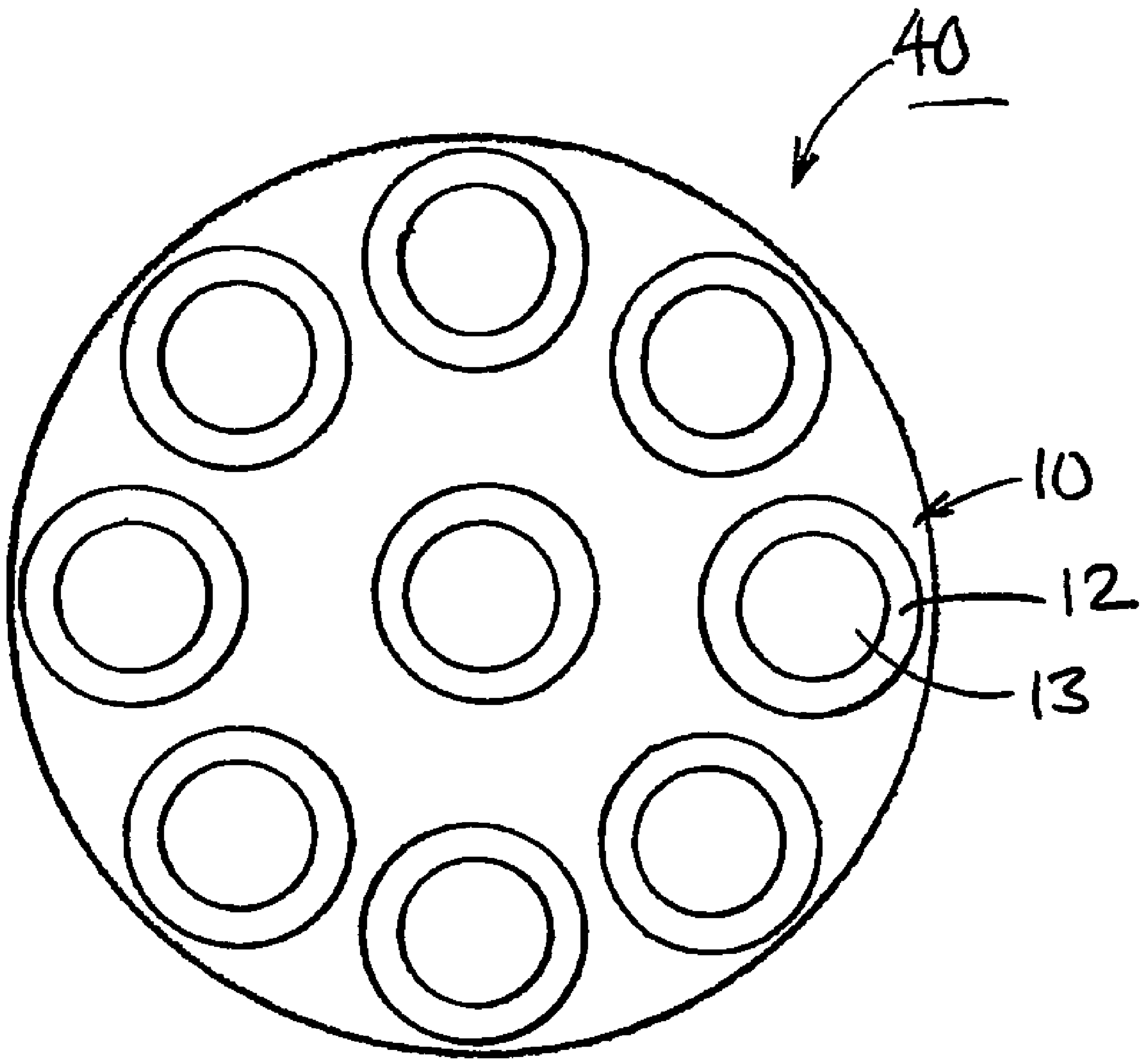
FIG. 32 presents a diagrammatic top view of parallel magnet units disposed in a circular arrangement.

FIG. 32 presents a multi-channel transfer device 40 in which the magnet units 10 are disposed in a circular array. Such a device is advantageous when micro-particles are to be collected from a large volume. Each one of the magnet units 10 may have a separate protective coating, but according to another embodiment a single protective coating is shared by all the magnet units 10.

The above-mentioned embodiments of the invention are only examples of implementation of the concept of the invention. It is obvious to the skilled person that different embodiments of the invention may vary in the scope of the claims presented below.

LIST OF REFERENCE NUMBERS

10 magnet unit
11 rod
12 ferromagnetic tube or sleeve
13 magnet
14 junction
15 end aperture
16 connecting tube
17 lines representing a magnetic field
18 collecting area of magnetic field
19 magnetic field
20 collecting surface
21 protective coating
22 micro-particles
23 solution
24 magnetic pole
25 liquid surface
26 vessel
27 winding
28 turning shaft
29 ridge in protective coating
30 micro-particle transfer device
31 frame tube
32 adapter sleeve
33 mounting flange
34 tube moving unit
35 tube moving pin
36 elongated slot
37 magnet motion slide
38 magnet moving pin
39 elongated slot
40 multi-channel device for transfer of micro-particles
41 magnet unit array
42 pocket
43 tie bar
44 return spring
45 connecting bar
46 “trigger”
50 automatic apparatus
51 matrix
52 control unit
53 arrow
54 arrow
55 sample plate
56 matrix (second time)
57 horizontal support
58 (second) control unit
60 reactor unit
61 reactor vessel or chamber
62 channel

63 valve
64 tip part
70 environmental cabinet
71 motor
72 actuator

The invention claimed is:

1. A magnetic transfer method for sorting, collecting, concentrating, transferring or dosing micro-particles (22) or magnetic particles either in the same liquid (23) or from one liquid (23*a*) into another (23*b*) by using a magnetic field, according to which method said particles are treated using a magnet unit (10) comprising a magnet (13) covered with a protective cover or coating (21) and a ferromagnetic tube (12), the magnet (13) and the ferromagnetic tube (12) being axially movable relative to each other for adjusting the magnetic field, the particles (22) are collected by using the magnet (13) covered with a protective cover or coating (21) so that when at least a part of the magnet is immersed in a liquid (23) the particles will gather on the surface of a protective cover or coating in an area (18) of a magnetic pole (24) of the magnet by means of magnetic field, the particles (22) are dosed by diminishing or removing the magnetic field by moving the magnet (13) inwards into the ferromagnetic tube (12) or moving the ferromagnetic tube over the magnet, said method being characterized as comprising using as said magnet, a magnet is selected from the group consisting of a magnet, which is provided with at least one magnet magnetized in the transverse direction of the longitudinal axis of ferromagnetic tube (12), a magnet (13), which is provided with at least one magnet magnetized in the direction of the longitudinal axis of ferromagnetic tube (12), a magnet, which is comprising several magnetic poles (24) in the same body, and a magnet (13), which is provided with individual magnets connected to each other or via suitable ferromagnetic or non-ferromagnetic adapters;

adjusting the collection surface area (18) on the surface of the protective cover or coating (21) by adjusting the length of the part of the magnet (13), which is protruding out from the ferromagnetic tube (12), when collecting the particles (22), at least one magnet (13) is used having at least two poles (24*a*, 24*b*) partly or completely outside the ferromagnetic tube (12) and below the surface (25) of the liquid (23), causing the particles to gather on the protective cover or coating (21) in the areas (18) close to the poles of the magnet or magnets, and when releasing or dosing the particles (22) the poles (24*a*, 24*b*) of the magnet (13) are partly or completely inside the ferromagnetic tube (12).

2. The method according to claim 1, wherein the particles (22) are collected using at least one magnet (13) magnetized in the transverse direction of the longitudinal axis of ferromagnetic tube (12), when collecting the particles (22) the poles (24*a*, 24*b*) being partly or completely outside the ferromagnetic tube (12) and below the surface (25) of the liquid (23), causing the particles to gather on the protective cover or coating (21) over the entire surfaces (18) of the poles of the magnet or magnets outside the ferromagnetic tube, and when releasing or dosing the particles (22) the poles (24*a*, 24*b*) of the magnet (13) are partly or completely inside the ferromagnetic tube (12).

3. The method according to claim 1, wherein the particles (22) are collected using at least one magnet (13) magnetized in the direction of the longitudinal axis of ferromagnetic tube (12), when collecting the particles (22), at least two poles (24*a*, 24*b*) of at least on magnet (13) are partly or completely outside the ferromagnetic tube (12) and below the surface (25) of the liquid (23), causing the particles to gather on the protective cover or coating (21) in the areas (18) of the poles of the magnet or magnets outside the ferromagnetic tube, and when releasing or dosing the particles (22) the poles (24*a*, 24*b*) of the magnet (13) are partly or completely inside the ferromagnetic tube (12).

4. The method according to claim 1, wherein the magnetic field is reduced by moving the ferromagnetic tube (12) over a magnet (13) placed inside a hard cup-like cover (21) or by pushing the tube into a space between an elastic protective coating and the magnet.

5. The method according to claim 1, wherein the microparticles (22) or magnetic particles are transferred by using a magnet (13), which is located in an aperture of a ferro-alloy plate (12), wherein the intensity of the magnetic field is adjusted by moving the magnet (13) and/or plate (12) in relation to each other.

6. A micro-particle (22) transfer device (10) for sorting, collecting, concentrating, transferring or dosing micro-particles or magnetic particles either in the same liquid (23) or from one liquid (23*a*) into another liquid (23*b*), said transfer device comprising a magnet unit (10) providing a magnet (13) covered with a protective cover or coating (21) and a ferromagnetic tube (12), the magnet (13) and the ferromagnetic tube (12) being axially movable relative to each other for adjusting the magnetic field, the magnet (13) having magnetic poles (24) and covered with a protective cover or coating (21) to be immersed in a liquid (23), for collecting particles on the surface of a protective cover or coating by means of magnetic field of the magnet, a ferromagnetic tube (12) for decreasing the magnetic field so that the magnet (13) is moved inwards into the tube or the ferromagnetic tube is moved over the magnet, wherein the transfer device (10) comprises as said magnet, a magnet selected from the group consisting of a magnet, which is provided with at least one magnet magnetized in the transverse direction of the longitudinal axis of ferromagnetic tube (12), a magnet (13), which is provided with at least one magnet magnetized in the direction of the longitudinal axis of ferromagnetic tube (12), a magnet, which is comprising several magnetic poles (24) in the same body, and a magnet (13), which is provided with individual magnets connected to each other or via suitable ferromagnetic or non-ferromagnetic adapters;

the collection surface area (18) on the surface of the protective cover or coating (21) and the length of the part of the magnet (13), which protrudes out from the ferromagnetic tube (12) is adjustable, at least one magnet (13) having at least two poles (24*a*, 24*b*) is partly or completely outside the ferromagnetic tube (12) and below the surface (25) of the liquid (23) when collecting the particles (22), causing the particles to gather on the protective cover or coating (21) in the areas (18) close to the poles of the magnet or magnets, and the poles (24*a*, 24*b*) of the magnet (13) are partly or completely inside the ferromagnetic tube (12) when releasing or dosing the particles (22).

7. The transfer device (10) according to claim 6, wherein the magnet (13) is magnetized in the transverse direction of the longitudinal axis of ferromagnetic tube (12), the poles (24*a*, 24*b*) are partly or completely outside the ferromagnetic tube (12) and below the surface (25) of the liquid (23) when the particles (22) are to be collected, causing the particles to gather on the protective cover or coating (21) over the entire surfaces (18) of the poles of the magnet or magnets being outside the ferromagnetic tube, and the poles (24*a*, 24*b*) of the magnet (13) are partly or completely inside the ferromagnetic tube (12) when releasing or dosing the particles (22).

8. The transfer device (10) according to claim 6, wherein the magnet (13) is magnetized in the direction of the longitudinal axis of ferromagnetic tube (12), at least two poles (24*a*, 24*b*) of the magnet (13) are partly or completely outside the ferromagnetic tube (12) and below the surface (25) of the liquid (23), causing the particles to gather on the protective cover or coating (21) in the areas (18) of the poles of the magnet or magnets being outside the ferromagnetic tube, and the poles (24*a*, 24*b*) of the magnet (13) are partly or completely inside the ferromagnetic tube (12) when releasing or dosing the particles (22).

9. The transfer device (10) according to claim 6, wherein the magnet (13) magnetized transversely is located in the aperture of the ferro-alloy plate (12), the magnet being adjustable so that the magnetic field or the intensity of the magnetic field of the magnet is proportional to the protruding part of the magnet.

10. The transfer device according to claim 6, wherein the ferromagnetic tube (12) is a cylinder and the magnet (13) is concentric with the ferromagnetic tube, the magnet (13) is magnetized in the transverse direction of the longitudinal axis of ferromagnetic tube (12) so that the poles (24*a*, 24*b*) of the magnet are on the sides of the magnet, and the magnet (13) is movable in the ferromagnetic tube (12) so that the magnet can be placed partly or completely outside the ferromagnetic tube or partly or completely inside the ferromagnetic tube.

11. The transfer device (10) according to claim 6, wherein the protective coating (21) is a cup-like body of non-stretchable material, such as hard plastic or metal, and the protective coating (21) forms an extension of the ferromagnetic tube (12) so that, when pushed out of the tube, the magnet (13) can move inside the protective coating.

12. The transfer device (10) according to claim 6, wherein the protective coating (21) is made of stretchable and elastic material which is stretched when the magnet (13) is being pushed out of the ferromagnetic tube (12).

* * * * *

UNITED STATES PATENT AND TRADEMARK OFFICE

CERTIFICATE OF CORRECTION

PATENT NO. : 7,622,046 B2
APPLICATION NO. : 10/531464
DATED : November 24, 2009
INVENTOR(S) : Rundt et al.

It is certified that error appears in the above-identified patent and that said Letters Patent is hereby corrected as shown below:

On the cover page,

Item [*] Notice: Subject to any disclaimer, the term of this patent is extended or adjusted under 35 U.S.C. 154(b) by 512 days.

Delete the phrase "by 512 days" and insert -- by 956 days --

Signed and Sealed this

Twenty-fourth Day of August, 2010

David J. Kappos

David J. Kappos
*Director of the United States Patent and Trademark Office*